(12) United States Patent
Margiott et al.

(10) Patent No.: US 12,383,170 B2
(45) Date of Patent: Aug. 12, 2025

(54) OXIMETER WITH STO2 AVERAGING

(71) Applicant: ViOptix, Inc., Newark, CA (US)

(72) Inventors: Alex Michael Margiott, Dunbarton, NH (US); William Welch, Sunnyvale, CA (US); Sushant Potdar, Fremont, CA (US)

(73) Assignee: ViOptix, Inc., Newark, CA (US)

( * ) Notice: Subject to any disclaimer, the term of this patent is extended or adjusted under 35 U.S.C. 154(b) by 0 days.

(21) Appl. No.: 18/389,604

(22) Filed: Dec. 19, 2023

(65) Prior Publication Data

US 2024/0115172 A1 Apr. 11, 2024

Related U.S. Application Data

(62) Division of application No. 17/146,201, filed on Jan. 11, 2021, now Pat. No. 11,844,612.

(60) Provisional application No. 62/959,808, filed on Jan. 10, 2020, provisional application No. 62/959,795, filed on Jan. 10, 2020.

(51) Int. Cl.
    *A61B 5/1455* (2006.01)
    *A61B 5/00* (2006.01)

(52) U.S. Cl.
    CPC ........ *A61B 5/14551* (2013.01); *A61B 5/6885* (2013.01); *A61B 5/742* (2013.01); *A61B 2503/10* (2013.01); *A61B 2503/40* (2013.01); *A61B 2560/0214* (2013.01); *A61B 2562/166* (2013.01)

(58) Field of Classification Search
    CPC ... A61B 5/0059; A61B 5/0205; A61B 5/1455; A61B 5/14551; A61B 5/14552; A61B 5/742; A61B 2560/0425; A61B 2562/166
    See application file for complete search history.

(56) References Cited

U.S. PATENT DOCUMENTS

| | | |
|---|---|---|
| 4,867,557 A | 9/1989 | Takatani et al. |
| 5,517,301 A | 5/1996 | Dave |

(Continued)

FOREIGN PATENT DOCUMENTS

| | | |
|---|---|---|
| TW | 200733936 A | 9/2007 |
| WO | 200212854 A2 | 2/2002 |

(Continued)

OTHER PUBLICATIONS

International Search Report, PCT Application PCT/US2021/013006, May 5, 2021, 13 pages.

*Primary Examiner* — Chu Chuan Liu
(74) *Attorney, Agent, or Firm* — Aka Chan LLP

(57) ABSTRACT

An oximetry device sealed in a sheath directs a user to allow the oximetry device to make oximetry measurements at a number of different tissue locations of a patient and average two or more of the oximetry measurements by directing the lifts and placements of the oximetry device and sheath to and from the different tissue locations and detecting the lift and placements. The averages are generated and displayed on a display of the device for the oximetry measurements if the lifts are made while use directions for the lifts are displayed on a display of the oximetry device. The averages are not generated if the lifts are not made while the user directions for the lifts are not displayed. The averages are simultaneously displayed with the oximetry measurements which are instantaneous measurement for patient tissue.

14 Claims, 27 Drawing Sheets

(56) References Cited

U.S. PATENT DOCUMENTS

| | | |
|---|---|---|
| 6,516,209 B2 | 2/2003 | Cheng et al. |
| 8,233,955 B2 | 7/2012 | Al-ali et al. |
| 8,750,954 B2 | 6/2014 | Petersen et al. |
| 8,798,700 B1 | 8/2014 | Heaton, II et al. |
| 9,398,870 B2 | 7/2016 | Bechtel et al. |
| 9,687,160 B2 | 6/2017 | Kiani |
| 10,722,156 B2 | 7/2020 | Lonsinger et al. |
| 2002/0161291 A1 | 10/2002 | Kianl et al. |
| 2003/0023151 A1* | 1/2003 | Khalil ............... A61B 5/1455 600/316 |
| 2006/0039139 A1 | 2/2006 | Maglica et al. |
| 2008/0015424 A1 | 1/2008 | Bernreuter |
| 2008/0319290 A1 | 12/2008 | Mao et al. |
| 2009/0018405 A1 | 1/2009 | Katsumura et al. |
| 2009/0253968 A1 | 10/2009 | Cho et al. |
| 2011/0205535 A1 | 8/2011 | Soller et al. |
| 2011/0224518 A1 | 9/2011 | Tindi et al. |
| 2011/0245639 A1 | 10/2011 | Gonopolskiy et al. |
| 2014/0046152 A1 | 2/2014 | Bechtel et al. |
| 2017/0303833 A1 | 10/2017 | Lonsinger et al. |
| 2017/0303835 A1 | 10/2017 | Bechtel et al. |
| 2017/0303861 A1 | 10/2017 | Bechtel et al. |
| 2019/0175084 A1 | 6/2019 | Bechtel et al. |

FOREIGN PATENT DOCUMENTS

| | | |
|---|---|---|
| WO | 2011008382 A1 | 1/2011 |
| WO | 2012100090 A2 | 7/2012 |
| WO | 2014/026200 A1 | 2/2014 |

\* cited by examiner

OXIMETER WITH STO2 AVERAGING

CROSS-REFERENCE TO RELATED APPLICATIONS

This application is a divisional of U.S. patent application Ser. No. 17/146,201, filed Jan. 11, 2021, issued as U.S. Pat. No. 11,844,612 on Dec. 19, 2023, which claims the benefit of U.S. patent applications 62/959,795 and 62/959,808, filed Jan. 10, 2020. These applications are incorporated by reference along with all other references cited in these applications.

BACKGROUND OF THE INVENTION

The present invention relates generally to optical systems that monitor parameters related to oxygen levels in tissue. More specifically, the present invention relates to optical probes, such as compact, handheld oximeters, and sheaths for the optical probes that shield the optical probes from contaminants during use and communicate status information to the optical probes regarding contaminant protection so that the optical probes are reusable.

Oximeters are medical devices used to measure the oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for a marathon); and veterinary purposes (e.g., animal monitoring).

In particular, assessing a patient's oxygen saturation, at both the regional and local level, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated hemoglobin, deoxygenated hemoglobin, melanin, water, lipid, and cytochrome. Oxygenated and deoxygenated hemoglobins are the dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving the reuse of oximeters; reducing or eliminating contamination during use; improving remote communication; improving measurement accuracy; reducing measurement time; lowering cost through reuse; reducing size, weight, or form factor; reducing power consumption; and for other reasons, and any combination of these.

Therefore, there is a need for improved tissue oximetry devices and methods of shielding oximetry devices during use for reuse of the devices.

BRIEF SUMMARY OF THE INVENTION

Embodiments relate to compact, handheld oximeters and sheaths that house and shield the handheld oximeters from contaminants during use. Because a handheld oximeter is located in a sheath and cannot contaminate patient tissue, the handheld oximeter can be reused.

In an implementation, a method includes detecting contact, by an oximetry device, of a first window of a sheath to first tissue of a patient, wherein the oximetry device is housed in the sheath and a display of the oximetry device is visible through a second window of the sheath, and making a first oximetry measurement of the first tissue using the oximetry device. The method includes generating a first oximetry value based on the first oximetry measurement, and displaying a first lift message on a display of the oximetry device. The method includes detecting, by the oximetry device, that the first window is moved out of contact with the first tissue, and detecting contact, by the oximetry device, of the first window of the sheath to second tissue of the patient, wherein the first and second tissues are different tissues. In an implementation, the first and second tissues are the same tissue so that oximetry measurements for the first and second tissues can be averaged to average out any contact variability on the tissue by the oximeter device. The method includes making a second oximetry measurement of the second tissue using the oximetry device, and generating a second oximetry value based on the second oximetry measurement.

The method includes displaying a first average of the first and second oximetry values on the display if the first window moved out of contact with the first tissue when the first lift message was displayed, and displaying the first oximetry value on the display if the first window moved out of contact with the first tissue when the lift message was not displayed on the display.

The averages are simultaneously displayed with the oximetry measurements for a least one tissue location where the oximetry measurement are instantaneous measurement for patient tissue.

The method allows for measurement averaging of oximetry measurements so that outlier measurements that may be displayed on the display can be assessed by a user in view of the average. Outlier measurements may give some concern to a user, but can be assessed in view of the average to determine whether the outlier measurements can be discarded. The average measurements also allow for averaging over a number of tissue locations of patient tissue so that a user of the oximetry device can assess overall health of the tissue (e.g., a tissue flap) being measured. The method can also help an inexperienced user learn how to make consistent contact of the tissue by the sheath or oximetry device so that inconsistent contact can be avoided. For example, the user can repeatedly contact the sheath or system unit onto a single tissue site and learn out to keep the average oximeter measurement constant by learning to consistently apply (e.g., apply with consistent pressure and uniform pressure across the window of the sheath or the probe face of the oximeter device) the sheath or system unit onto the tissue.

The handheld oximeters implementations are entirely self-contained, without any need to connect, via wires or wirelessly, to a separate system unit for making oximetry measurements. The sources and detectors of the oximetry device are arranged in an arrangement having various source-detector pair distances that allow for robust calibration, self-correction, and spatially-resolved spectroscopy in a compact probe. Other source-detector arrangements are also possible.

In an implementation, the handheld oximeter is a tissue oximeter that can measure oxygen saturation without requiring a pulse or heartbeat. A tissue oximeter of the invention is applicable to many areas of medicine and surgery, including plastic surgery. The tissue oximeter can make oxygen saturation measurements of tissue where there is no pulse; such tissue, for example, may have been separated from the body (e.g., a flap) and will be transplanted to another place in the body.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
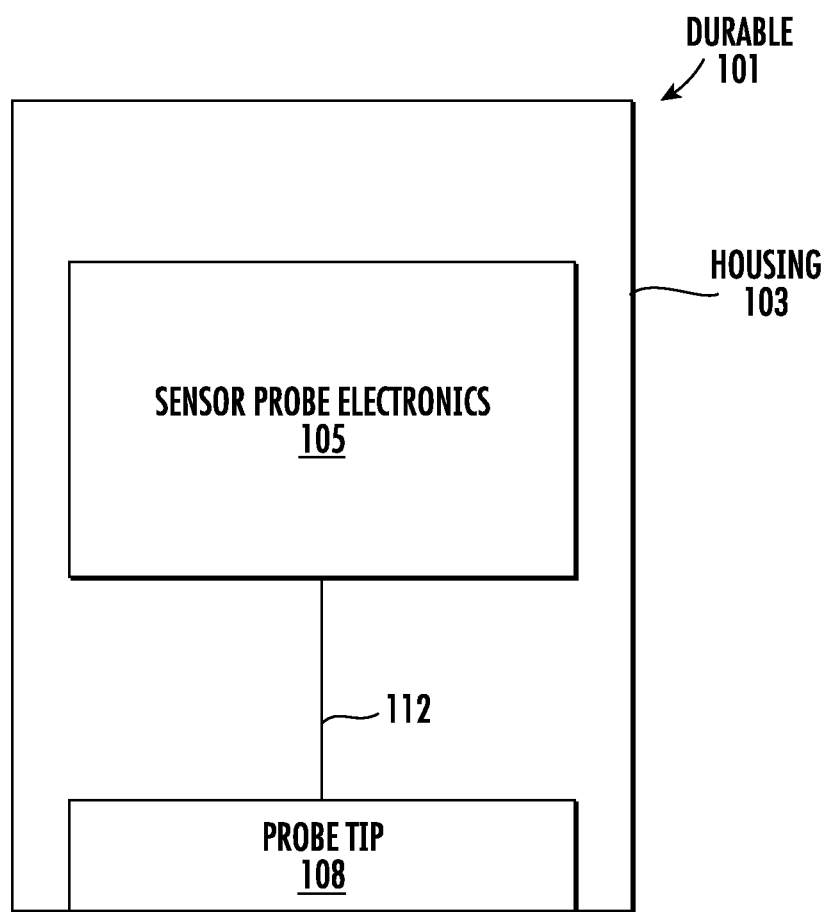
FIG. 1 shows a block diagram of a system unit for measuring various oximetry parameters of patient tissue.

Spectroscopy has been used for noninvasive measurements of various physiological properties in animal and human subjects. Visible (e.g., red light) and near-infrared spectroscopy is often utilized because physiological tissues have relatively low scattering in these spectral ranges. Human tissues, for example, include numerous light-absorbing chromophores, such as oxygenated hemoglobin, deoxygenated hemoglobin, melanin, water, lipid, and cytochrome. The hemoglobins are the dominant chromophores in tissue for much of the visible and near-infrared spectral range and via light absorption, contribute to the color of human tissues. In the visible and near-infrared range, oxygenated and deoxygenated hemoglobins have significantly different absorption features. Accordingly, visible and near-infrared spectroscopy has been applied to exploit these different absorption features for measuring oxygen levels in physiological media, such as tissue hemoglobin oxygen saturation (sometimes referred to as oxygen saturation) and total hemoglobin concentrations.

Various techniques have been developed for visible and near-infrared spectroscopy, such as time-resolved spectroscopy (TRS), frequency-domain techniques such as phase modulation spectroscopy (PMS), and continuous wave spectroscopy (CWS). In a homogeneous and semi-infinite model of physiological media, both TRS and PMS have been used to obtain the absorption coefficients and the reduced scattering coefficients of the physiological medium by use of the photon diffusion approximation, Monte Carlo models, or other techniques. From the absorption coefficients at multiple wavelengths, concentrations of oxygenated and deoxygenated hemoglobins can be determined and from these concentrations, the tissue oxygen saturation can be calculated.

Spatially-resolved spectroscopy (SRS) is one type of visible and near-infrared spectroscopy that allows tissue absorption to be determined independently from tissue scattering, thereby allowing absolute measurements of chromophore concentrations, such as oxygenated and deoxygenated hemoglobins. More specifically, an SRS instrument may emit light into tissue through a light source and collect the diffusely reflected light at two or more detectors positioned at different distances from the light source.

Alternatively, an SRS instrument may emit light from two or more light sources positioned at different distances from one or more detectors. Scattering of light back to the detectors is caused by relative changes of the index of refraction of the tissue and includes Mie scattering from larger structures such as mitochondria (the majority of tissue scattering is a result of mitochondria) and Rayleigh scattering from smaller structures such as intracellular vesicles. The absorption of light is caused by interaction with the tissue's chromophores.

From the reflectance (i.e., the recovered light intensity), which is recovered as a function of distance (e.g., multiple discrete distances of light detectors) from the light source, an SRS instrument can quantify the absorption coefficient and the scattering coefficient of the tissue at a single wavelength.

Multiple wavelengths of light can then be used with SRS to determine oxygenated and deoxygenated hemoglobin concentrations, and therefore, oxygen saturation within the volume of the tissue probed. Further, the wavelengths of the light source or light sources and the relative positions of the light source(s) with respect to a single detector or multiple ones of the detectors, allow tissue oximetry measurements to be made for a predetermined tissue depth.

One field in which visible and near-infrared spectroscopy, such as SRS, is useful is in tissue flap surgery in which a tissue flap is moved from one location on a patient to another location for reconstructive surgery. Visible and near-infrared spectroscopy techniques can be used to measure oxygen saturation in a tissue flap so that the viability of the tissue flap can be determined in surgery and after surgery. Intraoperative tissue flap oximetry probes that employ visible and near-infrared SRS should be able to quickly deliver accurate oxygen saturation measurements under a variety of nonideal conditions.

Oximetry probes adapted for SRS and other spectroscopies can come into contact with tissue, other surfaces, fluids (both liquid and gas), or other elements that can contaminate the probes. An oximetry probe that contacts tissue, for example, can be contaminated by the tissue, bacteria on the tissue, viruses on the tissue, tissue fluid, debris on the tissue, the environment near the tissue, any one of these substances, other substances, or any combination of these substances. A sheath can shield an oximetry probe from contaminants, but the efficacy of a sheath can be compromised in a number of ways. The ways in which a sheath can be compromised, allowing an oximetry probe to be contaminated, can be known and unknown. For example, a sheath housing an oximetry device may open and allow contaminants to contact the oximetry probe. The sheath opening may be relatively small and not detectable by visual inspection and the small opening may allow contaminants to enter the sheath and contact the oximetry probe. The efficacy of a sheath can be compromised if the sheath has been previously used and the previous use is unknown. The efficacy of a sheath can also be compromised if the sheath is provided from an unknown source and the sterility or sanitation of the sheath is unknown. Either inside or outside surfaces of the sheath, or both, can be contaminated if the sheath is provided by an unknown source. If the previous use of a sheath is unknown and the sheath is reused, contaminants on the sheath from an initial use can be spread during subsequent use of the sheath. Sheaths and the oximetry probes in the sheath may be contaminated in a variety of other ways. Reuse of an oximetry probe after contamination may be precluded or may increase the cost of reuse due to the cost of sanitizing or sterilizing the oximetry probe. Oximetry probes and sheaths of the present invention are directed toward improved sanitation, sterilization, or both.

FIG. 1 shows a system unit 101 for measuring various parameters of tissue in a patient. System unit 101 is sometimes referred to as a durable system unit because the unit is reusable, such as when the unit is used in combination with a protective sheath. The parameters of the tissue measured by the system unit may include an oxygen saturation level (relative oxygen saturation, absolute oxygen saturation, or both), a total hemoglobin concentration, an oxygenated hemoglobin concentration, an deoxygenated hemoglobin concentration, blood flow, pulse rate, a signal level of light reflected from the tissue, melanin concentration of tissue, other tissue parameters, or any combination of the parameters. The system unit includes housing 103, sensor probe electronics 105, and a probe tip 108, which is connected to the sensor probe electronics via a wired connection 112. Connection 112 may be an electrical connection, an optical connection, or another wired connection, including any number of wires (e.g., one, two, three, four, five, six, or more wires or optical fibers), or any combination of these or other types of connections. In other implementations, connection 112 may be a wireless connection, such as via a radio frequency (RF) or infrared (IR) connection.

Typically, the system unit is used by placing the probe tip in contact or close proximity to tissue (e.g., skin or internal organ or other tissue) at a site where tissue parameter measurements are desired. The system unit causes an input signal to be emitted by the probe tip into the tissue (e.g., human tissue). There may be multiple input signals, and these signals may have varying or different wavelengths of electromagnetic radiation. The input signal is transmitted into the tissue and reflected from the tissue, absorbed by the tissue, or transmitted through the tissue.

Then, after transmission through the tissue or reflection from the tissue, the signal is received at the probe tip. This received signal is received and analyzed by the sensor probe electronics. Based on the received signal, the sensor probe electronics determine various parameters of the tissue, such as an oxygen saturation level, a total hemoglobin concentration, an oxygenated hemoglobin concentration, an deoxygenated hemoglobin concentration, a blood flow, a pulse, a signal level of light reflected from the tissue, melanin concentration of tissue, or other tissue parameters. One or any combination of these parameters can be displayed on a display screen of the system unit.

In an implementation, the system unit is a tissue oximeter, which can measure oxygen saturation and hemoglobin concentration, without requiring a pulse or heartbeat. A tissue oximeter of the invention is applicable to many areas of medicine, surgery (including plastic surgery and spinal surgery), post-surgery, athlete monitoring, and other uses. The tissue oximeter can make oxygen saturation and hemoglobin concentration measurements of tissue where there is no pulse, such as tissue that has been separated from the body (e.g., a tissue flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. There are various implementations of systems and techniques for measuring oxygen saturation, such as discussed in U.S. patent applications 62/959,757, 62/959,764, 62/959,778, and 62/959,787, filed Jan. 10, 2020; Ser. No. 17/146,176, 17/146,182, 17/146,186, 17/146,190, 17/146,194, and 17/146,197, filed Jan. 11, 2021; and Ser. No. 29/720,112, 29/720,115, 29/720,120, and 29/720,122, filed Jan. 9, 2020. These patent applications are incorporated by reference along with all other references cited in these applications.

Figure 2:
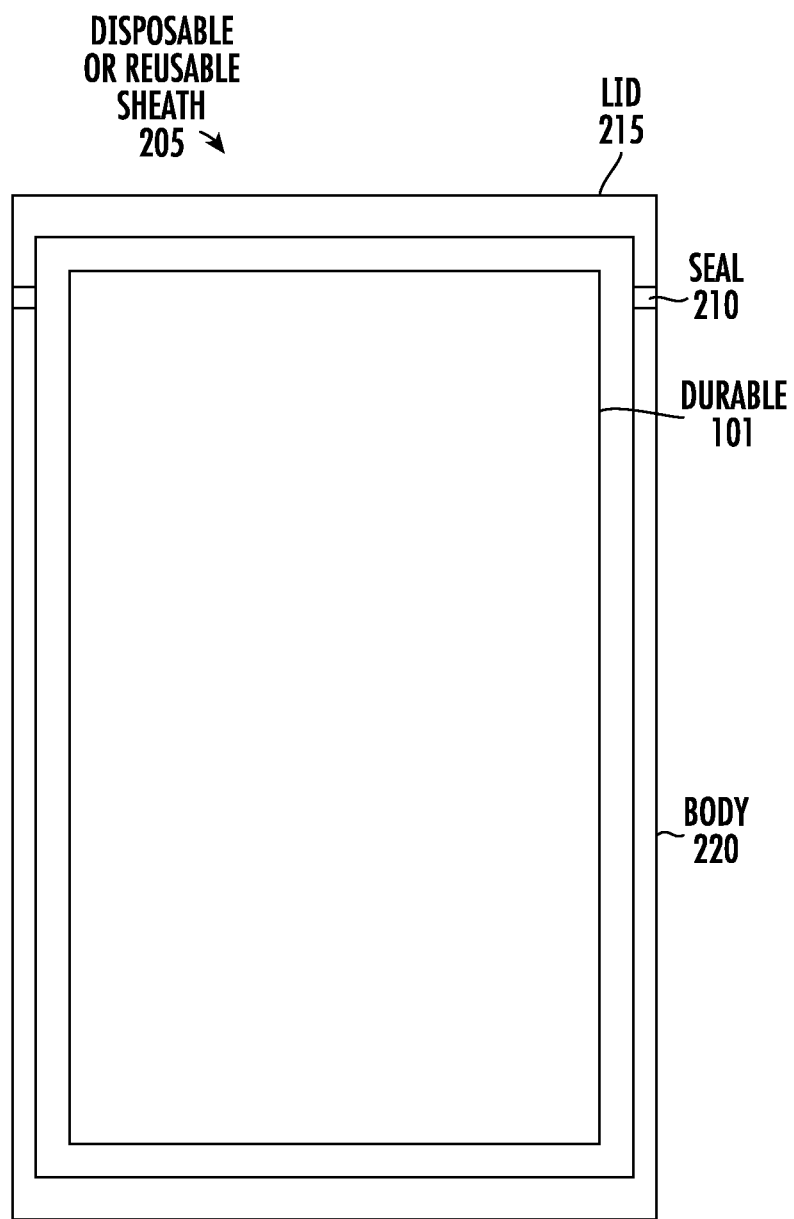
FIG. 2 shows a block diagram of the system unit housed in a sheath.

FIG. 2 shows system unit 101 housed in a sheath 205. The sheath includes a lid 215 and a body 220, which may be sealed to the lid via a seal 210. The lib may be separable from the body or may be connected to the body, such as via a hinge. The hinge may allow the lid to rotate to seal the lid to the body. The sheath may be a disposable sheath or a sheath that is reusable. For example, the system unit and sheath may travel with a patient from surgery (e.g., use) to post-surgery (e.g., reuse) for tissue monitoring.

With the lid opened, the system unit may be inserted into the sheath, and thereafter the lid may be sealed to the body to house and seal the system unit in the sheath. The system unit may then be used to make tissue parameter measurements in the sealed environment provided by the sheath. The sheath can protect the system unit from contacting elements that the sheath contacts, such as tissue, tissue fluid, biological agents (e.g., bacteria, viruses, prions, and pyrogens), debris, and other contaminants. When the lid is open and the seal is broken, the system unit may be removed from the sheath. Because the system unit is sealed into the sheath by the body, lid, and seal, the system unit can remain relatively clean, sanitized, or sterile for reuse.

The sheath can also protect the tissue of a patient from contacting elements that are on a system unit that is inside the sheath. The sheath can prevent patient tissue from contacting bacteria, viruses, prions, pyrogens, other contaminants, or anyone of these contaminants that might be on the system unit from passing through the sheath seal and contacting patient tissue.

Figure 3:
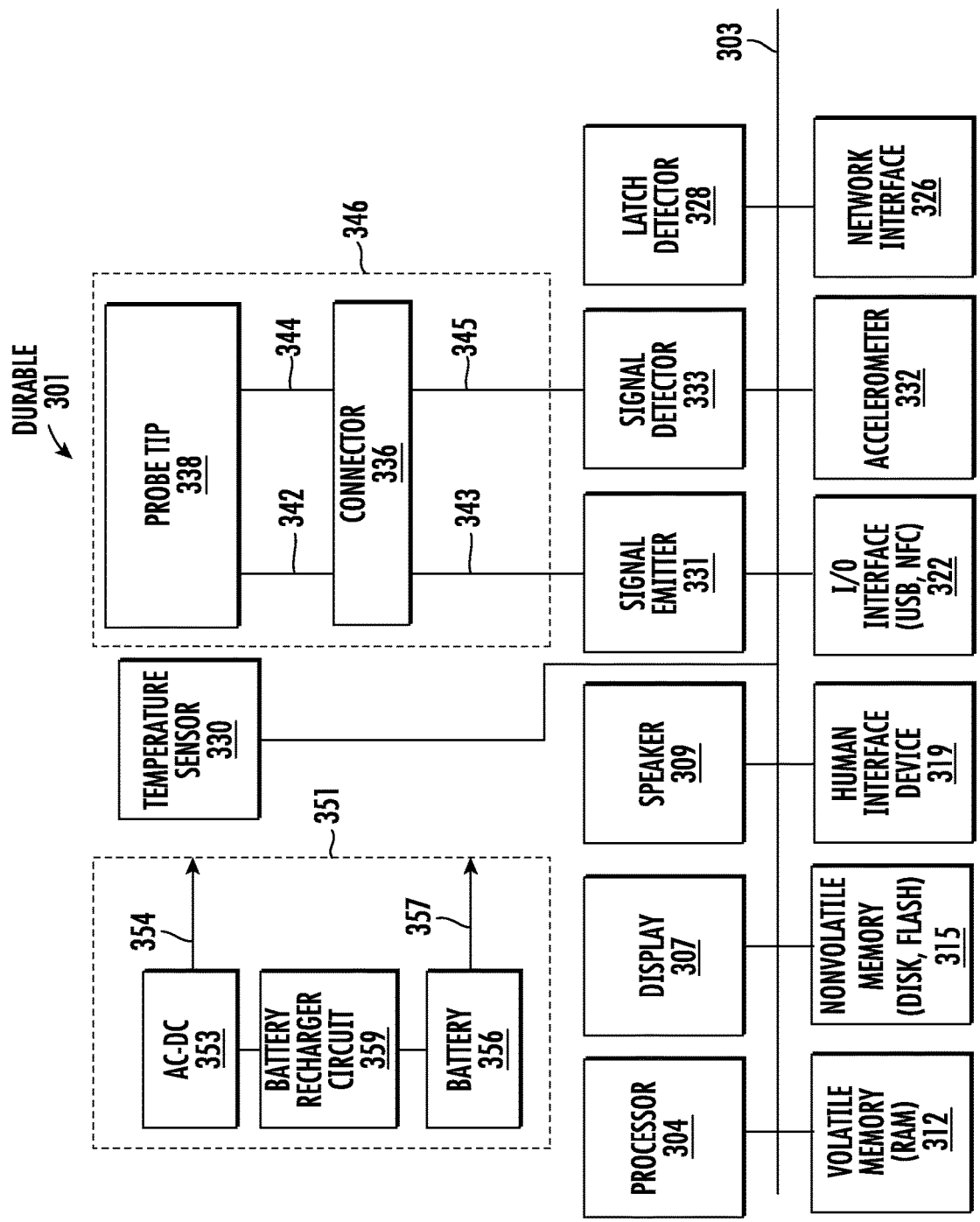
FIG. 3 shows a block diagram of the system unit, in an implementation.

FIG. 3 shows a block diagram of system unit 301, in an implementation. The system unit includes a processor 304, display 307, speaker 309, signal emitter 331, signal detector 333, volatile memory 312, nonvolatile memory 315, human interface device (HID) 319, input-output (I/O) interface 322, network interface 326, latch detector 328, temperature sensor 330, and accelerometer 332. These components are housed within housing 103. Different implementations of the system may include any number of the components described, in any combination or configuration, and may also include other components not shown.

The components are linked together via a bus 303, which represents the system bus architecture of the system unit. Although FIG. 3 shows one bus that connects to each component of the system unit, bus 303 is illustrative of any interconnection scheme that links the components of the system unit. For example, one or more bus subsystems can interconnect one or more of the components of the system unit. Additionally, the bus subsystem may interconnect components through one or more ports, such as an audio port (e.g., a 2.5-millimeter or 3.5-millimeter audio jack port), a universal serial bus (USB) port, or other port. Components of the system unit may also be connected to the processor via direct connections, such as direct connections through a printed circuit board (PCB).

In an implementation, system unit 301 includes a sensor probe 346. The sensor probe includes a probe tip 338 and a connector 336. The probe tip is connected to the connector via a first communication link 342 and a second communication link 344. First communication link 342 may include an electrical wire, a set of electrical wires (e.g., a ribbon cable), a waveguide (e.g., fiber optic cable), a set of waveguides (e.g., a set of fiber optic cables), a wireless communication link, or any combination of these types of links. The second communication link may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The electrical wire or sets of electrical wires of the first communication link, the second communication link, or both can include one or more electrical traces on a printed circuit board.

The connector connects (e.g., removably connects) the probe tip, the wires, waveguides, or any combination of these elements to the signal emitter and signal detector of the system unit. For example, a communication link 343 may connect the signal emitter to the connector and a communication link 345 may connect the signal detector to the connector. Each of the communication links 343 and 345 may include an electrical wire, a set of electrical wires (e.g., a ribbon cable) one waveguide, a set of waveguides, a wireless communication link, or any combination of these links. Each communication link can also include one or more electrical traces on a printed circuit board. For example, the connector may include one or more connectors that are mounted on a PCB. Communication links 342, 344, or either one of these links may be ribbon cables that connect to the probe tip and connect to connectors mounted on a PCB. In this implementation, communication links 343 and 345 can be electrical traces on the PCB that link to the single emitter, signal detector, or both. In this implementation, the signal emitters and signal detectors may be electrical emitters and detectors that control light emitters, light detectors, or both in the probe tip.

In an implementation, where the probe tip is separable from the system unit 301, connector 336 may have a locking feature, such as an insert connector that may twist or screw to lock. If so, the connector is more securely held to the system unit and it will need to be unlocked before it can be removed. This will help prevent the accidental removal of the probe tip from the system unit.

The connector may also have a first keying feature, so that the connector can only be inserted into a connector receptacle of the system unit in one or more specific orientations. This will ensure that proper connections are made.

The connector may also have a second keying feature that provides an indication to the system unit a type of probe (e.g., a probe from many different types of probes) that is attached. The system unit may be adapted to make measurements for a number of different types of probes. When a probe is inserted in the system unit, the system uses the second keying feature to determine the type of probe that is connected to the system unit. Then the system unit can perform the appropriate functions, use the appropriate algorithms, or otherwise make adjustments in its operation for the specific probe type.

In an implementation, signal emitter 331 includes one or more light sources that emit light at one or more specific wavelengths. In a specific implementation, the light sources emit five or more wavelengths of light (e.g., 730 nanometers, 760 nanometers, 810 nanometers, 845 nanometers, and 895 nanometers). Other wavelengths of light are emitted by the light sources, including shorter and longer wavelengths of light in other implementations. The signal emitter may include one or more laser diodes or one or more light emitting diodes (LEDs).

In an implementation, signal emitter 331 is an emitter that emits electrical signals to one or more light sources, which may emit light based on the received electrical signals. In some implementations, the signal emitter includes one or more light sources and electrical signal emitters that are connected to the light sources.

In an implementation, signal detector 333 includes one or more photodetectors capable of detecting the light at the wavelengths produced and emitted by the signal emitter. In another implementation, the signal detector 333 is an electrical signal detector that detects electrical signals generated by one or more photodetectors. In another implementation, the signal detector includes one or more photodetectors and one or more electrical detectors that are connected to the photodetectors.

In an implementation, HID 319 is a device that is adapted to allow a user to input commands into the system unit. The HID may include one or more buttons, one or more slider devices, one or more accelerometers, a computer mouse, a keyboard, a touch interface device (e.g., a touch interface of display 307), a voice interface device, or another HID.

In an implementation where the HID is an accelerometer and the system unit is a handheld unit, the accelerometer may detect movements (e.g., gestures) of the system unit where the system unit may be moved by a user. Movements may include a left movement, right movement, forward movement, back movement, up movement, down movement, one or more rotational movements (e.g., about one or more axes of rotation, such as the x-axis, y-axis, z-axis, or another axis), any combinations of these movements, or other movements.

Information for the various movements detected by the accelerometer may be transmitted to the processor to control one or more systems of the system unit. For example, an upward movement (e.g., a lifting movement) may be transmitted to the processor for powering on the system unit. Alternatively, if the system unit is set down and left unmoved for a predetermined period of time, then the processor may interpret the lack of movement detected by the accelerometer as a standby mode signal and may place the system unit in a standby power mode (a lower power mode than a normal operation mode where oximetry measurements can be made by the system unit), or a power-down signal and may power down the system unit.

When the system unit is powered on, information for a left movement or a right movement detected by the accelerometer and transmitted to the processor may be used by the processor to control the system unit. For example, a left or right movement of the system unit may be used by the processor to change menu items displayed on the display. For example, the processor may use the information for a left movement to scroll menu items on the display to the left (e.g., scroll a first menu item left and off of the display to display a second menu item on the display). The processor may use the information for a right movement of the system unit to scroll menu items to the right (e.g., scroll a first menu item right and off of the display, and display a second menu item on the display).

The HID and processor may be adapted to detect and use various movements to activate a menu item that is displayed on the display. For example, information for an upward movement or a downward movement may be detected and used to activate a menu item that is displayed on the display. For example, if a user is prepared to take an oximeter measurement and a menu option is displayed for taking an oximeter measurement, a quick downward movement of the system unit may start a measurement when the probe tip is placed in contact with tissue The HID may include one or more accelerometers to detect motion in various directions (e.g., linear, rotational, or both). The accelerometers can include one or more capacitive micro-electro-mechanical system (MEMS) devices, one or more piezoresistive devices, one or more piezoelectric devices, or any combination of these devices.

In an embodiment, accelerometer 332 is adapted to detect relatively high G-force accelerations associated with a shock that the system unit experiences. The shock may be from bumping the system into something, dropping the system unit (e.g., dropping the system unit on a table or the floor), or other shock events. In an implementation, if the accelerometer indicates to the processor that a shock event has occurred, the processor can take a number of actions. For example, the processor can shut down the system unit. The processor can display one or more messages on the display. The messages may indicate that the system unit should be recalibrated. The message may indicate that contact between the system unit and the sheath should be checked. The accelerometer may include one or more capacitive micro-electro-mechanical system (MEMS) devices, one or more piezoresistive devices, one or more piezoelectric devices, or any combination of these devices.

In an implementation, the latch detector 328 is adapted to detect whether a latch of the sheath is latched or unlatched. If the latch is latched, then the system unit is housed and enclosed in the sheath. In this configuration, with the system unit housed and enclosed in the sheath, the system unit may not be contaminated by material contacting the outside surface of the sheath. If the latch is unlatched and the system unit is in the sheath, then the system unit might be contaminated with material contacting the outside surface of the sheath. That is, the seal that seals the lid of the sheath to the body of the sheath may be unsealed (i.e., opened) and contaminates may pass from outside of the sheath to the inside of the sheath where the system unit is located.

In an implementation, at least a first portion of the latch is metal. Other portions of the latch may be metal or other material, such as a plastic material. The first portion of the latch is a first distance from the latch detector when the latch is latched and is a second distance from the latch detector when the latch is unlatched. The first distance is less than the second distance.

In an implementation, the latch detector includes an inductor that can inductively couple to the first portion of the latch. The inductor can be driven with a direct current or an alternating current and thus detect when the first portion of the latch moves toward the latch detector or away from the latch detector. The latch detector can be calibrated so that the latch detector can detect when the latch moves to the first distance away from the latch detector or farther than the first distance away from the latch detector. The latch detector can include an analog-to-digital converter, a digital signal processor (DSP), or both that digitize and analyze the current flowing through the inductor. One or both of these circuits can communicate the digitalized information to the processor that can determine whether the latch is open or closed. The processor can display a message on the display to indicate whether the latch is open or closed, whether the seal for the sheath is sealed or unsealed, warn of potential contamination, or other messages associated with the latch being opened or closed.

In an embodiment, the latch detector is a capacitive detector that can capacitively couple to the latch. The capacitive detector can detect the latch in the latched position at a first distance from the capacitive detector and moving away from the latched position and the first distance.

The nonvolatile memory 315 may include a FLASH memory, other nonvolatile solid-state storage (e.g., USB flash drive), battery-backed-up volatile memory, tape storage, reader, and other similar media, and combinations of these. In some implementations, the nonvolatile memory includes a mass disk drive, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc). The volatile memory may include a random access memory (RAM).

The processor may include a microcontroller, a microprocessor, an application specific integrated circuit (ASIC), programmable logic (e.g., field programmable gate array), or any combination of these circuits. The processor may include multiple processors or a multicore processor, which may permit parallel processing of information.

In an implementation, the system unit is part of a distributed system. In a distributed system, individual systems are connected to a network and are available to lend resources to another system in the network as needed. For example, a single system unit may be used to collect results from numerous sensor probes at different locations.

Aspects of the invention may include software executable code, firmware (e.g., code stored in a read only memory (ROM) chip), or both. The software executable code or firmware may embody algorithms used in making oxygen saturation measurements of the tissue. The software executable code or firmware may include code to implement a user interface by which a user uses the system, displays results on the display, selects or specifies parameters that affect the operation of the system, or execute algorithms and calculations to generate a result.

Further, a computer-implemented or computer-executable version of the invention may be embodied using, stored on, or associated with a computer-readable medium. A computer-readable medium may include any medium that participates in providing instructions to one or more processors for execution. Such a medium may take many forms, including but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, MATLAB (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows XP, Windows XP x64 Edition, Windows Vista, Windows CE, Windows 7, Windows 8, Windows 10, Windows Mobile), Linux, HP-UX, UNIX, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may communicate with other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or another device (e.g., a laptop computer, smartphone, or personal digital assistant), a user accesses the system unit of the invention through a network such as the Internet. The user will be able to see the data being gathered by the system unit. Access may be through the World Wide Web (WWW). The Web browser is used to download Web pages or other content in various formats, including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
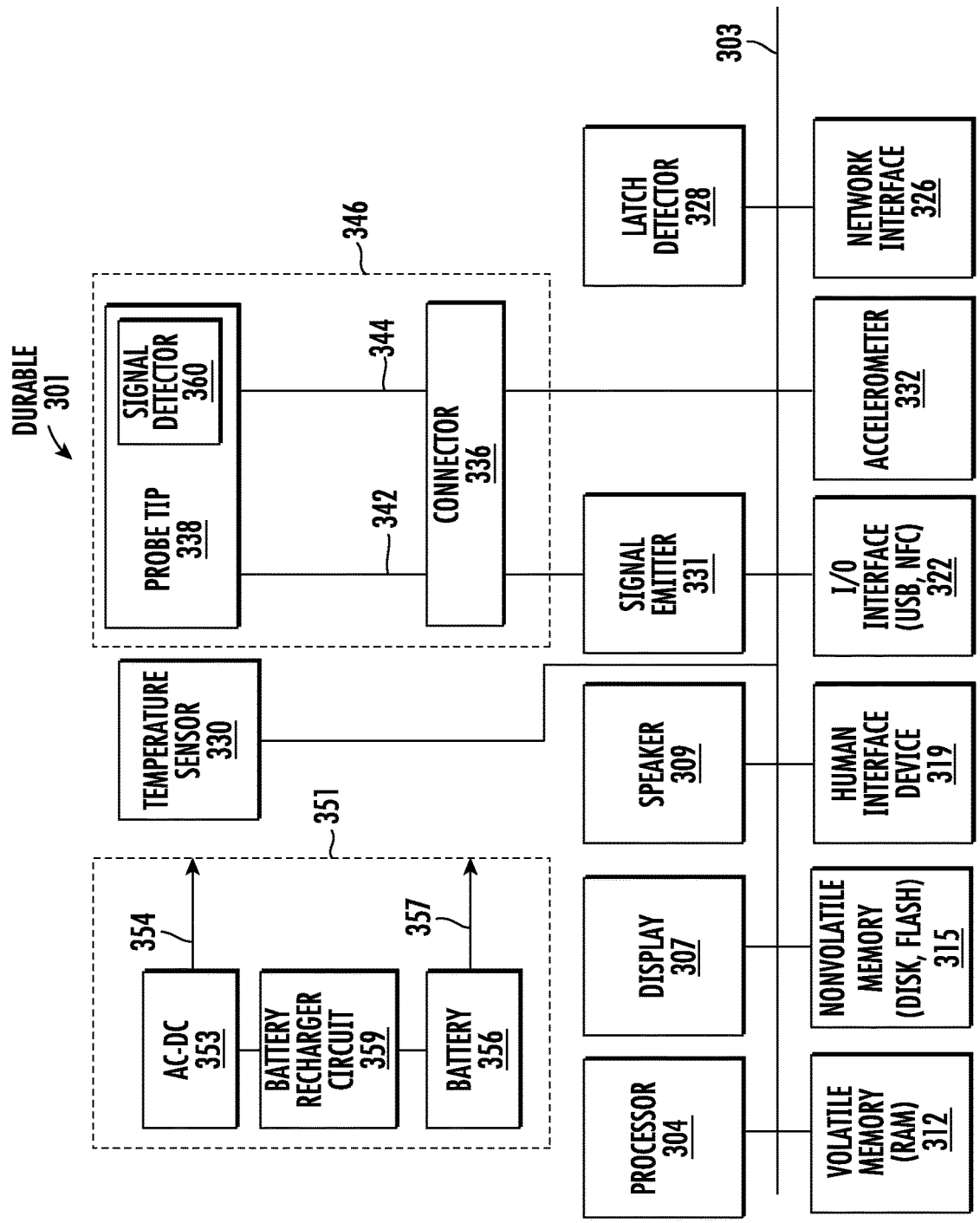
FIG. 4 shows a block diagram of the system unit, in an implementation.

FIG. 4 shows a block diagram of system unit 401, in an implementation. System unit 401 is similar to system unit 301 but differs in that the signal detector 344 is located in probe tip 346. A wire or set of wires (e.g., a ribbon cable) may connect the signal detector to the bus and processor. For example, a ribbon cable that is connected to the signal detector may also be connected to a connector or socket mounted on a PCB that the processor and other circuits are mounted on. The signal detector may be located at a probe face of the probe tip. The signal emitter may be optically located behind the probe face of the probe tip.

Figure 5:
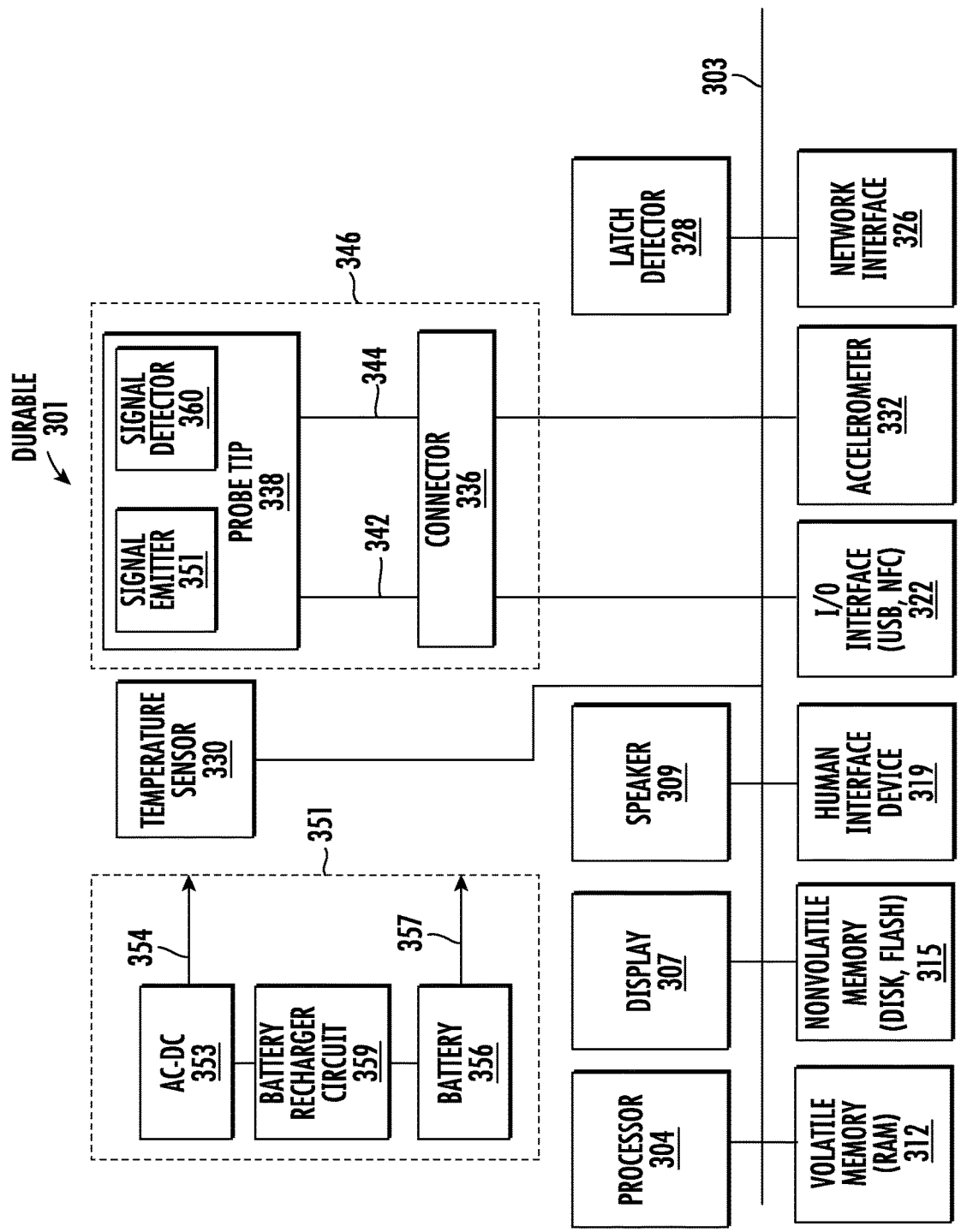
FIG. 5 shows a block diagram of the system unit, in an implementation.

FIG. 5 shows a block diagram of system unit 501, in an implementation. System unit 501 is similar to system units 301 and 401 but differs in that the signal emitter 331 and the signal detector 344 are located in probe tip 346. A wire or wires (e.g., one or more ribbon cables) may connect the signal emitter, the signal detector, or both to the bus and processor. A first ribbon cable may connect the signal emitter to the bus and processor and a second ribbon cable may connect the signal detector to the bus and processor. For example, the first ribbon cable that is connected to the signal emitter may also be connected to a connector or socket mounted on a PCB that the processor and other circuits are mounted on, and the second ribbon cable that is connected to the signal detector may also be connected to a connector or socket mounted on the PCB. The signal detector may be located at a probe face of the probe tip. The signal emitter may be optically located behind the probe face of the probe tip.

In an implementation, connector 336 includes a locking feature, such as an insert connector that inserts into a connecting port and then twists or screws to lock. If so, the connector is more securely held to the system unit and it will need to be unlocked before it can be removed. This will help prevent accidental removal of the probe.

In an implementation, connector 336 includes one or more PCBs that are connected to one or more wires (e.g., ribbon cables) that connect to the signal emitter, the signal detector, or both. For example, a first ribbon cable may connect to a first PCB that connects to the signal emitter. A second ribbon cable may connect to a second PCB that connects to the signal detector.

Block 351 shows a power block of the system unit having both AC and battery power options. In an implementation, the system includes an AC-to-DC converter 353, such as a full-wave rectifier. The converter takes AC power from a wall socket, converts AC power to DC power, and the DC output is connected (indicated by an arrow 354) to the components of the system unit needing power.

In an implementation, the system is battery operated. The DC output of a battery 356 is connected (indicated by an arrow 357) to the components of the system unit needing power. The battery may be recharged via a recharger circuit 359, which received DC power from the AC-to-DC converter. The AC-to-DC converter and recharger circuit may be combined into a single circuit. In an implementation, the battery is rechargeable via magnetic charging or induction charging.

In an implementation, block 351 is a battery module that includes one or more batteries that power the components of the system unit. The batteries may be rechargeable or disposable batteries. The block may not include the AC-to-DC converter. Block 351 may be a block that is integrated with the system unit or is separable from the system unit.

Figure 6:
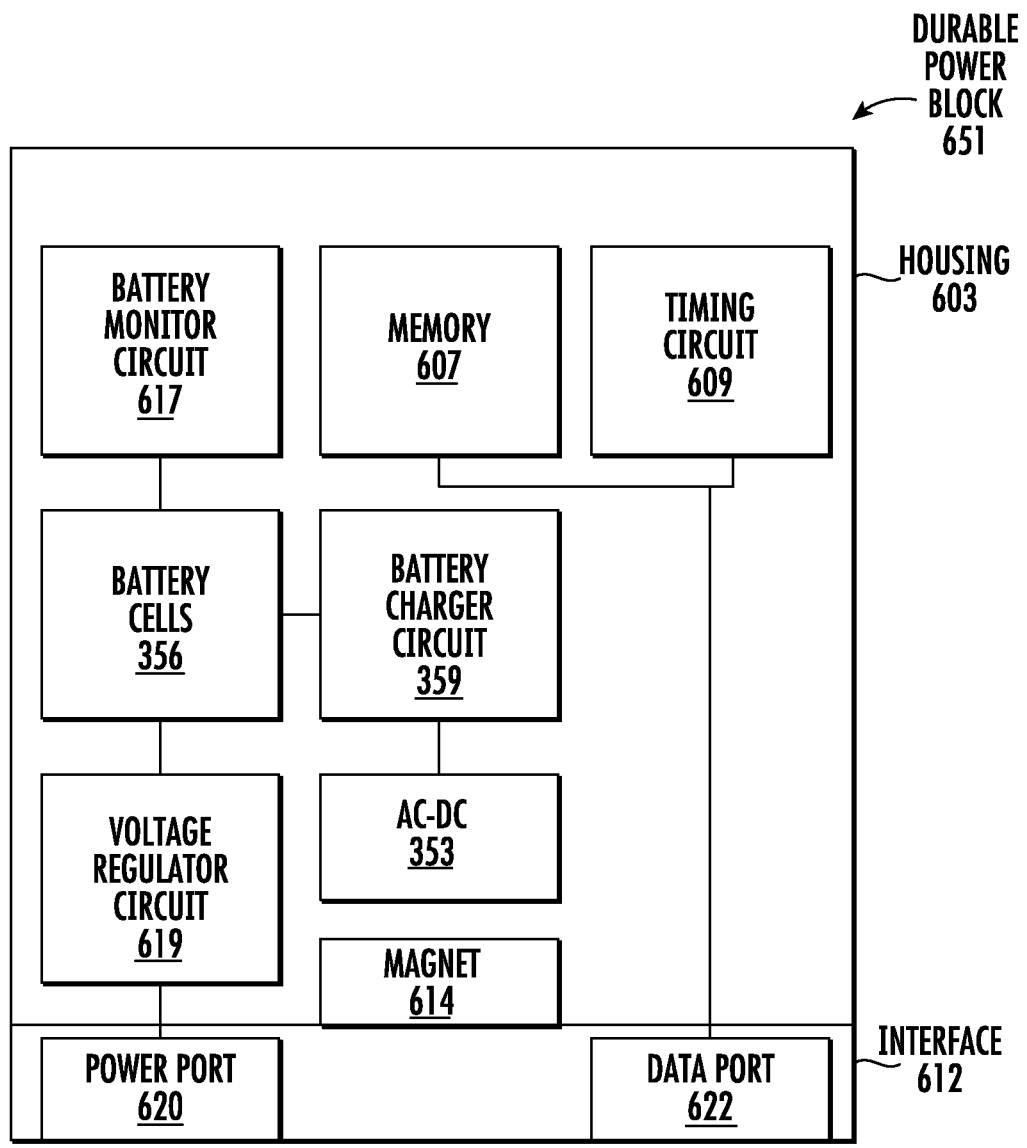
FIG. 6 shows a diagram of the power block of the system unit, in an implementation.

FIG. 6 shows block 651 that is a power block, in an implementation. Block 651 is similar to block 351 but may include a battery monitor 617, a voltage regulator circuit 619, a memory 607, a timing circuit 609, an interface 612, which includes a power port 620 and a data port 622, a magnet 614, other circuits, or any combination of these circuits.

Battery monitor 617 may be connected to the battery cells 356 and may monitor the capability of the battery cells. For example, the battery monitor may determine a current charge state, such as a percentage of the total possible charge. The battery monitor may determine the charge capacity of the battery cells. The charge capacity may be a percentage of the charge capacity compared to the charge capacity of the battery cells when new. The battery monitor may determine the maximum power delivery capability of the battery.

The battery cells may be disposable battery cells, such as alkaline battery cells, or rechargeable battery cells, such as nickel-metal hydride, lithium battery cells (e.g., Li/FeS2 size AA, AAA, N, CR123, 18650, or others), lithium polymer, or other types of cells. The power back may include four battery cells that are AA size cells that output 1.5 volts. The four batteries may be in series to output 6 volts, or may be in series and parallel to output 3 volts.

Voltage regulator circuit 619 may be connected between the battery cells and the power port of the battery interface 612. The voltage regulator circuit conditions the voltage output from the battery to output an approximately constant voltage. The voltage regular circuit may also include a DC-to-DC converter that converts a first voltage output from the battery cells to a second voltage that is different from the first voltage.

The timing circuit is a circuit that determines the amount of time length that the battery has been used. Information for the amount of time may be stored in the memory and may be transferred through the data port to the processor when the processor queries the memory for the information.

In an embodiment, the memory may also store an encrypted identifier that identifies the power block. The processor may be adapted to retrieve the encrypted identifier via the power blocks data port. The processor or another decryption circuit of the system unit may decrypt the encrypted identifier and may identify the power block based on the identifier after decryption. The identifier may identify the manufacturer of the power block or may identify other information about the power block, such as the manufacturing date, the battery cell type, battery cell voltage, elapsed usage time, or any combination of these elements. In an implementation, if the identifier is not a known identifier that is known to the system unit, then the processor with not allow the system unit to operate with the power block. That is, the system unit will not operate with a power block manufactured by an unknown manufacturer. Allowing the system unit to operate with known (e.g., authorized) power blocks, the system unit is assured that the power provided by the power block is within the operating specifications of the system unit. Therefore, the circuits, signal emitters, signal detectors, and other elements of the system unit will operate within predetermined parameters and will not operate outside of the predetermined parameters. Also, using a known battery from a known manufacturer provides that the stem unit will operate for a known period of time so that the system unit will not run out of battery power during a medical procedure, such as a surgery. Operating the system unit according to predetermined parameters, facilitates the system unit making accurate and reliable oximetry measurements.

In an implementation, nonvolatile memory 315 stores one or more identifiers for one or more power blocks that may operate with the system unit. The processor may compare the identifier for the power pack that has been decrypted to the one or more identifiers retrieved from the nonvolatile memory to determine whether the power block will be allowed to operate with the system unit. If the power block is not authorized for use with the system unit, the processor may cause a message to be displayed on the display that indicates that the power block is not authorized for use with the system unit. If the power block is authorized to operate with the system unit, then the system unit may operate to make oximetry measurements without displaying information on the display about the authenticity or the inauthenticity of the power block.

In an implementation, the memory of the power block stores an indicator that indicates whether the battery has been previously used. The indicator may be the time information for the amount of time that the power block has operated. A nonzero use time stored in the memory is an indicator that the power block has been previously used. Alternatively, the indicator may be an identifier of a system unit that the power block has been connected to and provided power to. For example, the nonvolatile memory of the system unit may store an identifier of a system unit. The processor of the system unit may transfer the system identifier of the system unit to the power block for storage in the power block's memory. In an implementation, the system unit tests the battery use by a threshold that is greater than zero (e.g., usage number stored in the battery's memory), to handle the case of someone accidentally disconnecting the battery before insertion into the sheath. If the system unit checked a usage of zero versus nonzero, then the battery would be rejected for use for the accidental battery disconnection situation. A threshold greater than zero allows for the system unit test to not interrupt the workflow of connecting the battery and placing the battery in the sheath. That is, the implementation attempts to ensure that a power block is fully charged and can be used for the duration of a medical procedure (e.g., a surgery) without the power block running out of stored energy. Ensuring that a power block is unused prior to using the power block during a medical procedure provides that the power block will not run out of power during the procedure and minimize risk to a patient. That is, patient risk is lowered if a system unit used during a procedure does not run out of power and can be used for patient monitoring when required.

In an implementation, when the power block is attached to a system unit, the processor of the system unit may query the power block's memory to retrieve the time information for the amount of time that the power block has operated. In an implementation, if the system unit determines that the power block has been previously used based on the time information, then the system unit will not operate with the power block. Similar to the embodiment described immediately above, ensuring that a power block is unused prior to using the power block during a medical procedure provides that the power block will not run out of power during the procedure and minimize risk to a patient.

When the power block is attached to a system unit, the processor of the system unit may query the power block's memory to retrieve any system identifier that may be stored in the power block's memory. In an implementation, if a system identifier retrieved from the power block's memory is different from the system identifier of the system unit that is retrieved the system unit from the power block's memory, then the system unit will not operate with the power block.

The power block may include one more magnets 614 that are arranged in an arrangement, such as a square, a rectangular, or another arrangement. A system unit may also have one or more magnets or one or more metal plates (e.g., ferromagnetic plates) that are arranged in an arrangement that is complementary to the arrangement of magnets in the power block. The magnets of the power block may attract the magnets or metal plates of the system unit when the power block is placed in contact with the system unit. The magnetic attraction between the magnets or plates may hold the power block in place when the system unit is being used.

The power block may include one more plates (e.g., ferromagnetic plates) that are arranged in an arrangement, such as square, rectangular, or another arrangement. The system unit may include one or more magnets that are arranged in a complementary arrangement. The magnets of the system unit may magnetically attract the metal plates of the power block when the power block is placed in contact with the system unit. The magnetic attraction between the magnets and plates may hold the power block in place when the system unit is being used.

In an implementation, the power port of the power block includes at least two electrical contacts (e.g., a power contact and a ground contact) and the data port includes at least two electrical contacts (e.g., a data line and a shared ground contact with the power port). The electrical contacts are arranged in an arrangement, such as in a row, in a square, in a rectangle, another arrangement. The system unit includes a power port that includes at least two electrical contacts (e.g., a power contact and a ground contact) and includes a data port that includes at least two electrical contacts (e.g., a data line and a shared ground contact with the power port). The arrangement of the electrical contacts is complementary to the electrical contacts of the power block.

When the power block is placed in contact with the system unit, the magnetic attraction between the magnets or between the magnets and metal plates forces the electrical contacts of the power port in the system unit into contact with the electrical contacts of the power port of the power block. Also, the magnetic attraction forces the electrical contacts of the data port in the system unit into contact with the electrical contacts of the data port of the power block. As such, electrical power can be transferred from the power block to the system unit to power the circuits and other elements of the system unit, and data can be transferred between the power block and the system unit.

Figure 7:
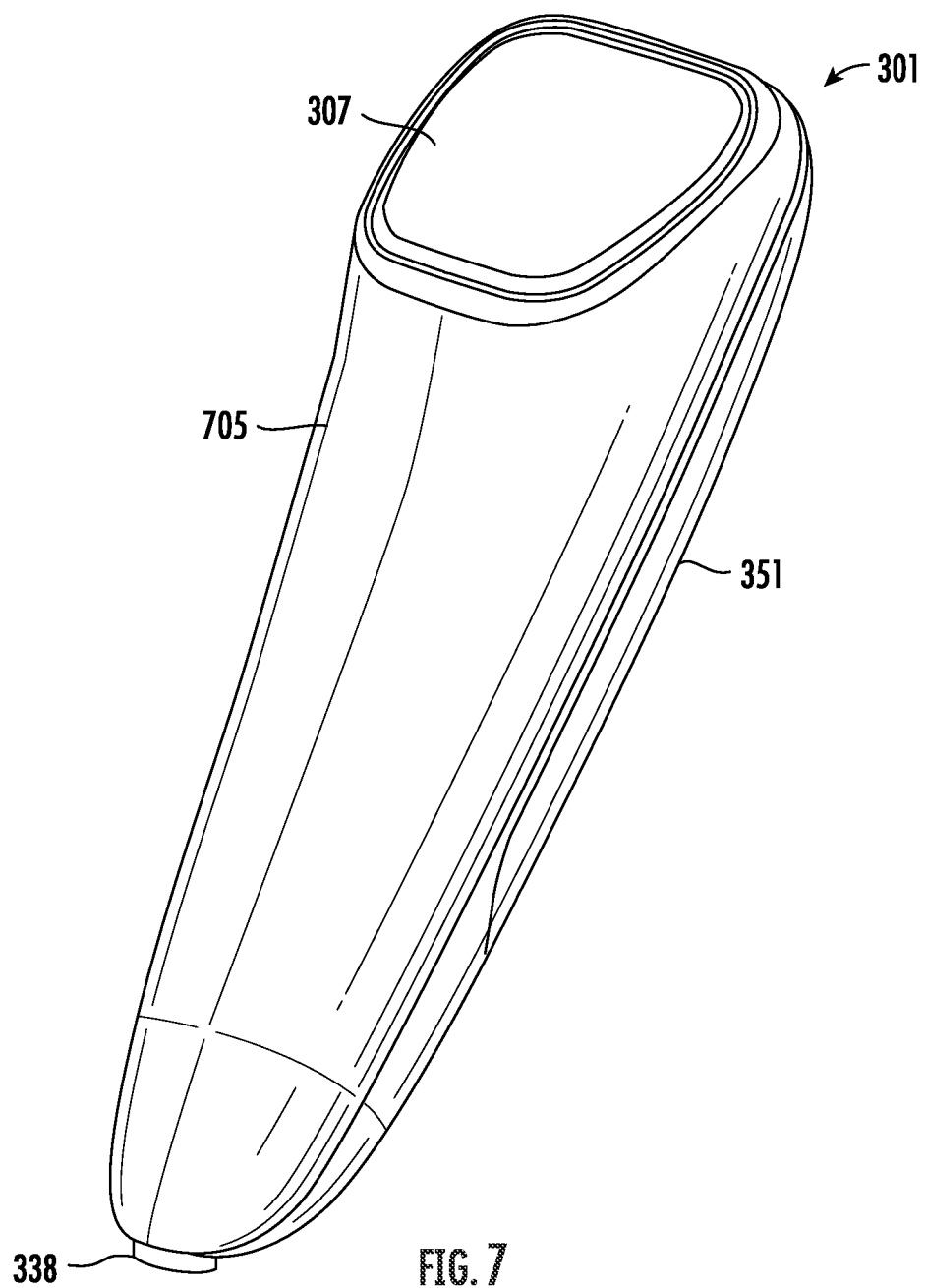
FIG. 7 shows a perspective view of the system unit and power block.

FIG. 7 shows a perspective view of the system unit 301 and power block 351 coupled to the system unit, in an implementation. Display 307 of the system unit is located at a first end of the system unit and the probe tip 338 is located at a second end of the system unit where the first and second ends of proximal and distal ends of the unit. The housing of the system unit tapers from the first end to the second end. The described circuit elements are housed in housing 705 of the system unit. When the second window of the sheath is in contact with tissue, the first window of the sheath and the display of the system unit faces away from the tissue for easy visibility of the display. In an implementation where the system unit is used without a sheath, when the probe face of the system unit is in contact with tissue, the display faces away from the tissue for easy visibility of the display.

Figure 8:
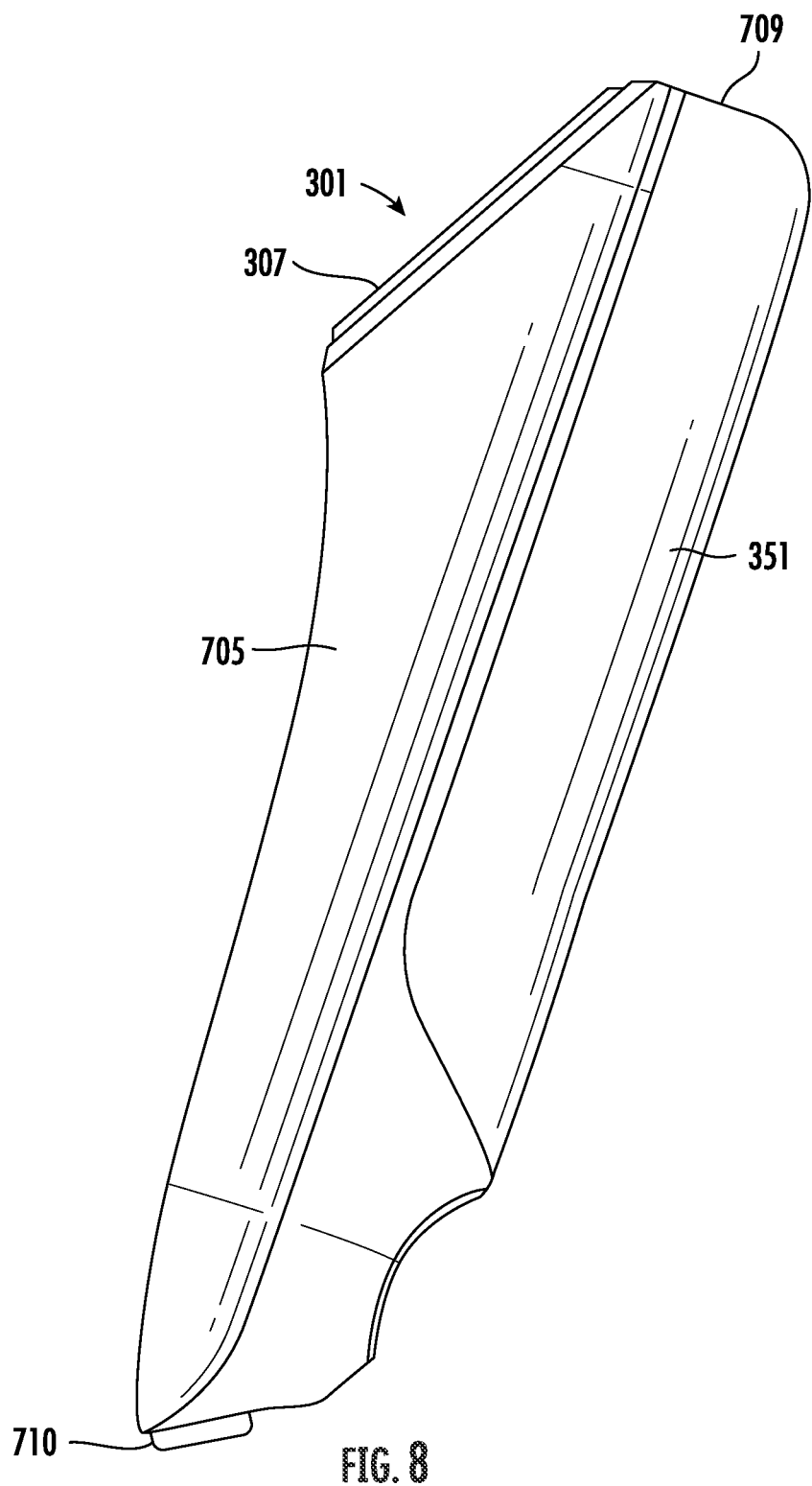
FIG. 8 shows a side view of the system unit.

FIG. 8 shows a side view system unit 301, in an implementation. The housing 705 of the system unit includes a bezel 710 that houses a portion of the probe tip. The bezel includes an opening the exposes a probe face of the probe tip.

Figure 9:
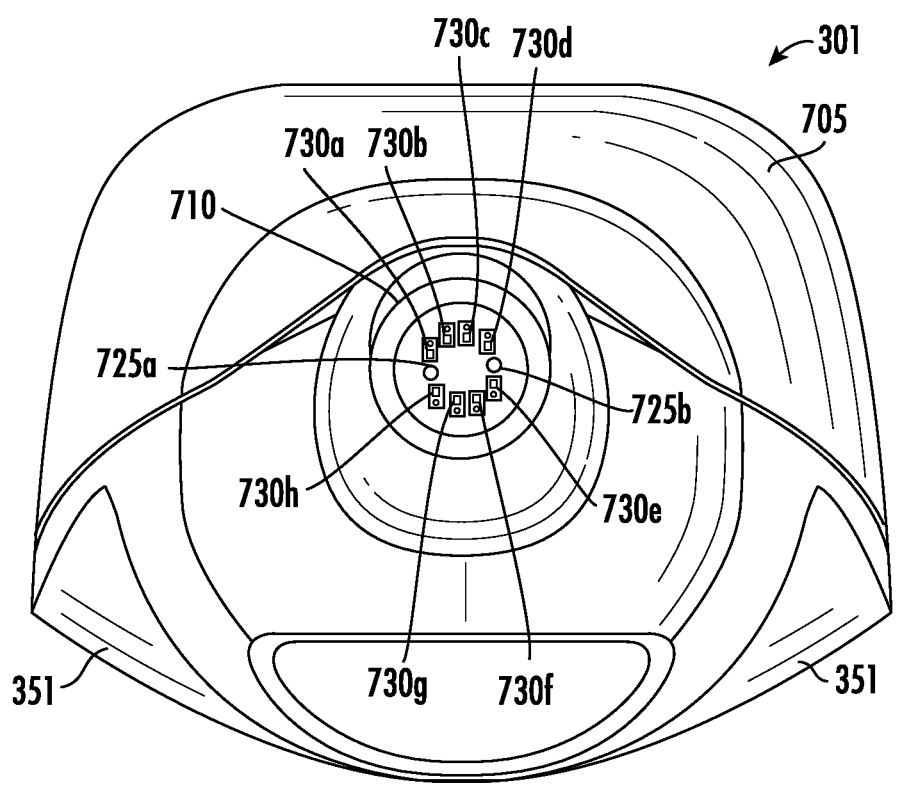
FIG. 9 shows an end view of the system unit.

FIG. 9 shows an end view of the second end of the system unit, in an implementation. The end of bezel 710 is shown with the probe face 715 in the opening of the bezel. The probe face may include an aperture plate 720 that includes a number of source apertures, for example, source apertures 725*a* and 725*b*, and includes a number of detector apertures 730*a*-730*h*. Each of the source apertures may be included in a source structure that may include light sources, such as one or more optical fibers, laser diodes, LEDs, one or more portions of the aperture plate, or other structures at the probe tip in any combination. Each of the detector apertures may be included in a detector structure that may include light detectors, such as one or more optical fibers, photodetectors, one or more portions of the aperture plate, or other structures at the probe tip in any combination.

Figure 10A:
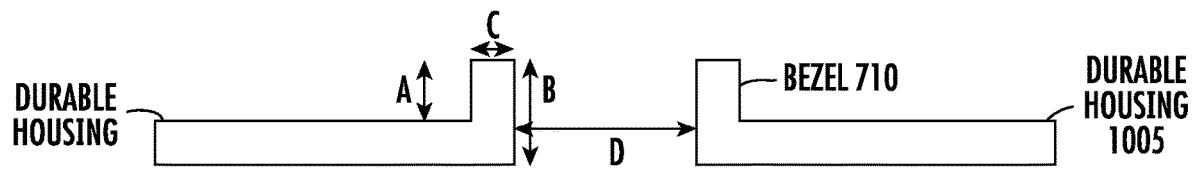
FIGS. 10A-10D show a number of steps for forming the probe face of the probe tip and forming the finished bezel of the housing of the system unit.

FIGS. 10A-10D show a number of steps for forming the probe face 715 of the probe tip 338 and forming the finished bezel 710 of the housing 1005 of the system unit 301. FIG. 10*a* shows the bezel 710 of the housing 1005 at an initial height A where the height is from the outside surface of the housing to the top of the bezel. Height A may be from about 3.5 millimeters to about 4 millimeters. In a specific implementation, height A is about 3.75 millimeters. The inner height B of the bezel is from the inside surface of the housing to the top of the bezel. Height B may be from about 4.5 millimeters to about 5.5 millimeters. In a specific implementation, height B is about 5.05 millimeters. The diameter D of the opening of the bezel may be from about 8 millimeters to about 10 millimeters. In a specific implementation, the diameter of the opening of the bezel may be about 9.1 millimeters. The width C of the bezel at the bezel's end may be about 1.0 millimeters to about 2.0 millimeters. The width C may vary around the circumference of the bezel. In a specific implementation, the width C of the bezel is about 1.5 millimeters.

Figure 10B:
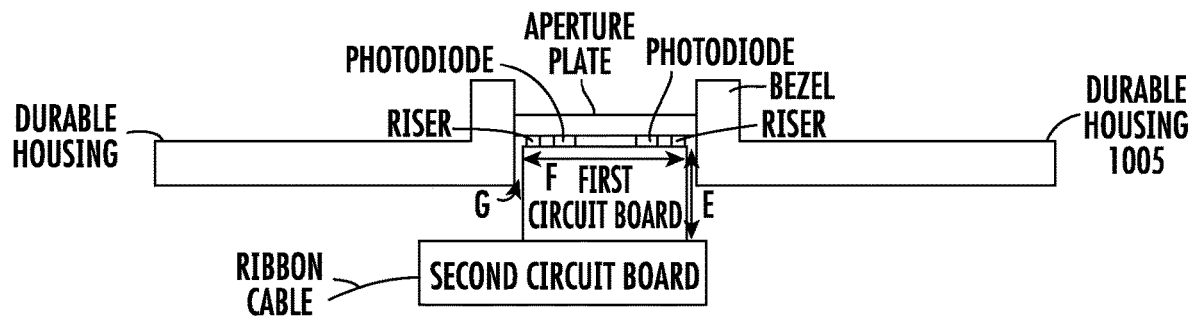

FIG. 10B shows the housing and bezel with a portion of the probe tip 338 in the housing and bezel. The portion of the probe tip shown includes a first circuit board 1020, a second circuit board 1025, riser 1030, photodiodes 1035, an aperture plate 1040, and a ribbon cable 1045 connected to the second circuit board. The first and second circuit boards may include electrical traces that are coupled. The second circuit board may be a fiberglass circuit board (e.g., FR4) that includes electrical traces that are connected to electrical traces of the first circuit board. The electrical traces of the first circuit board may extend upward from the second circuit board along the outer surface of the first circuit board. The first and second circuit boards may be connected by mechanical fasters, plastic welding, an adhesive (e.g., epoxy), another material, or any combination of these materials. The first circuit board may have a diameter F of about 6 millimeters to about 8 millimeters. In a specific implementation, the diameter F of the first circuit board is about 7 millimeters. The first circuit board may have a height E of about 3 millimeters to about 4 millimeters. In a specific implementation, the height E of the first circuit board is about 3.5 millimeters.

A distance G between the side of the first circuit board and the inner sidewall of the bezel may be about 0.5 millimeters to about 1.5 millimeters. In a specific embodiment, the distance between the side of the first circuit board and the inner sidewall of the bezel may be about 1.05 millimeters.

The riser may be connected to both the first circuit board and the aperture plate and may separate the first circuit board and aperture plate may be predetermined height. The photodiodes may be mounted on a top surface of the first circuit board and be connected to the electrical traces of the first circuit board. The aperture plate may include an aperture for each photodiode that is mounted on the first surface of the first circuit board and the diodes may respectively be inside the apertures. The height of each riser may be about 100 micrometers to about 200 micrometers. In an implementation, the height of each riser is about 150 micrometers.

Figure 10C:
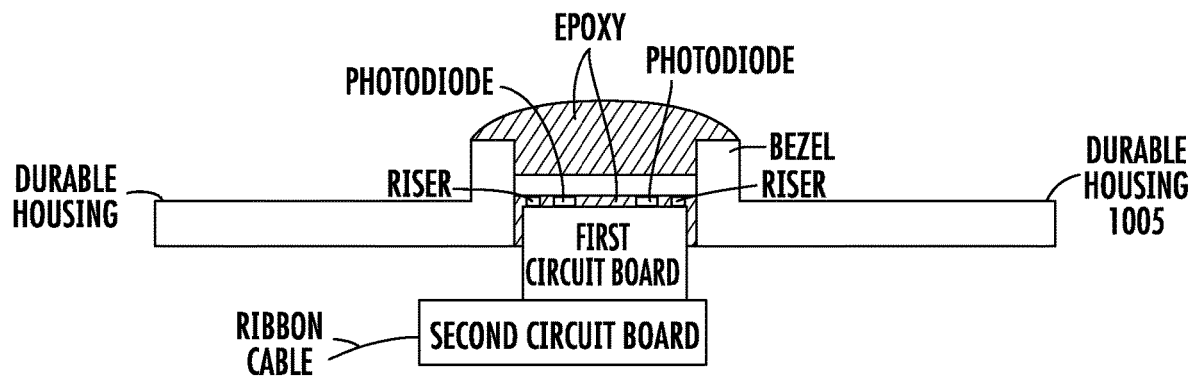

After the portion of the probe tip shown in FIG. 10B is placed into the opening of the bezel, epoxy is flowed into the opening as shown in FIG. 10C. The epoxy may flow into the apertures of the aperture plate, along the sides of the first circuit board, and may flow to the second circuit board and around the sides of the second circuit board.

Figure 10D:
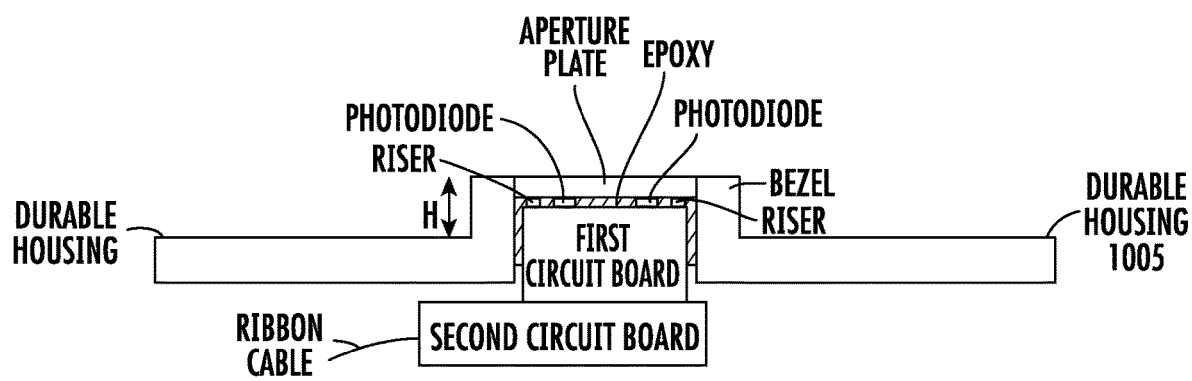

After the epoxy cures, the epoxy and a portion of the side of the bezel may be removed (e.g., polished down) to a final height, as shown in FIG. 10D. The final outside height H of the bezel may be about 2.0 millimeters to about 3 millimeters. In a specific implementation, the final outside height H of the bezel is about 2.58 millimeters. In an implementation, a portion of the aperture plate may also be thinned (e.g., polished thinner) when the bezel and epoxy are removed. The aperture plate can include a marker embedded in the plate. The embedded marker is exposed and polished away in the polishing process, the polishing is completed when the marker is polished away.

In an implementation, the epoxy is polished down to the surface of the tops of the photodetectors inside the apertures of the aperture plate. In another implementation, a thin layer of epoxy remains over the tops of the photodiodes after polishing.

Figure 11:
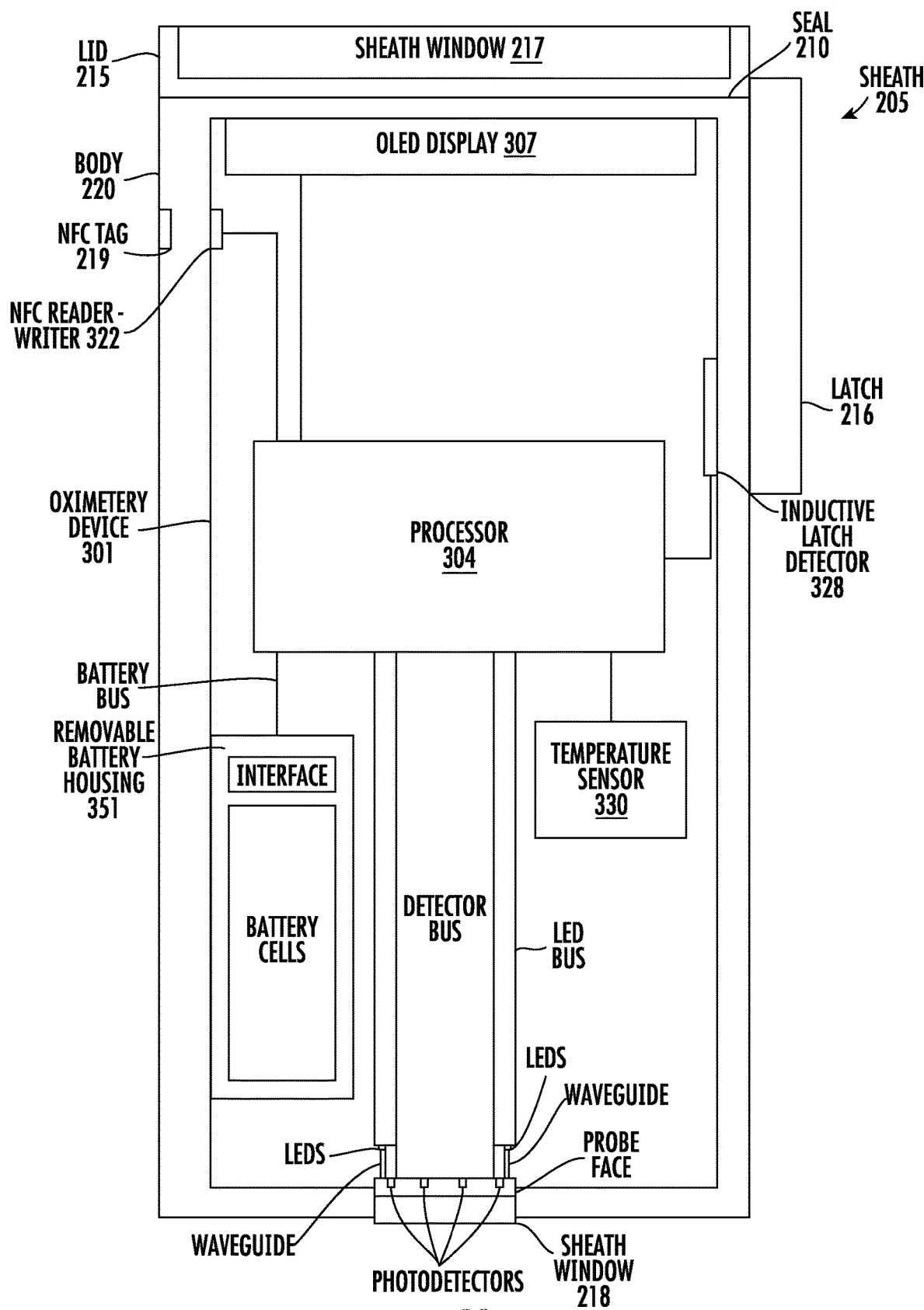
FIG. 11 is a block diagram of the system unit in a sheath, in an implementation.

FIG. 11 is an additional block diagram of system unit 301 in sheath 205, in an implementation. The sheath includes the seal 210, the lid 215, the body portion 220, a latch 216, a first sheath window 217, a second sheath window 218, and a radio-frequency communication device 219, such as an NFC tag. The sheath may include a hinge that hinge couples the lid to the body portion and allows the lid to be opened and closed. Both the lid and sheath can be formed of a relatively rigid plastic material.

As described above, the latch latches that lid closed and seals the seal. The latch also releases the lid from the closed position and allows for the seal to be unsealed. The latch detector 328 (e.g., an inductor or a capacitive detector and an A-to-D converter coupled to the processor) of the system unit is positioned nearest to the latch when the latch is closed (i.e., the first distance from the latch detector) so that the latch detector can detect when the latch is latched, the lid is closed, and the seal is sealed. That latch detector can detect when the latch opens and moves away from the first distance.

In an implementation, a first portion of the latch is rigidly connected to the lid and a second portion of the latch extends in a cantilever configuration from the lid. The first and second portions are opposite portions of the latch. The latch is capable of bending to latch that latch to the body of the sheath and bending to unlatch the latch from the body. The latch can be steel, such as spring steel, which allows the second portion (e.g., cantilevered portion) of the latch to bend to latch and unlatch the latch from the body.

In an implementation, a first portion of the latch is rigidly connected to the body and the second portion of the latch extends in a cantilever configuration from the lid. The latch capable of bending to latch that latch to the lid of the sheath and unlatch the latch from the lid.

The latch can be hinge connected to the lid via a lid hinge. With the lid hinge connected to the lid, that latch can rotate towards the body of the sheath and away from the body of the sheath to latch that latch to the body and unlatch the latch from the body. In another implementation, the latch is hinge connected to the body of the sheath and can rotate towards the lid and away from the lid to latch to the lid and unlatch from the lid.

In an implementation, the first window 217 is located in the lid of the sheath. The first window is positioned over display 307 (e.g., an organic LED display) of the system unit when the lid of the sheath is closed. The first window can be transparent so that information displayed on the display is visible and discernable to a user when the lid of the sheath is closed. The first window can be a plastic material or glass. The first window can be sealed to the lid via an adhesive, such as epoxy, an O-ring, welding, heat-stake (if both materials are plastic), or another seal material. The seal can prevent contaminants (e.g., patient tissue, patient fluid, or other debris) from passing through the seal and contaminating the system unit. The sheath window may be a square-shaped window or a rectangular window that approximately matches the size and shape of display 307.

The second window 218 can be at an opposite end of the sheath from the first window. The second window can contact the probe face of the probe tip when the system unit is in the sheath. The second window can have a relatively flat surface that contacts the polished probe face so that relatively little air is trapped between the second window and the probe face when the second window and probe face are in contact. In an implementation, the inside surface (e.g., inside the body of the sheath) of the second window can have an adhesive that can stick to the probe face of the system unit.

In an implementation, the I/O interface 322 of the system unit includes an NFC reader-writer. The NFC reader-writer can power the NFC tag 219 of the sheath so that the NFC reader-writer can communicate with the NFC tag. In some implementations, the NFC tag is battery powered by a battery of the NFC tag or of the sheath. In an implementation, the NFC tag is a read only NFC tag where information can be read from the NFC tag by the NFC reader-writer of the system unit. In an implementation, the NFC tag can be read and can be written to by the NFC reader-writer.

In an implementation, the NFC tag includes a memory (e.g., a non-volatile memory, a random access memory, or both) that can store an identifier for the sheath, store an indicator that indicates whether the sheath has been previously used or is unused, other information, or any combination of this information. The identifier for the sheath can be an unencrypted identifier or an encrypted identifier that is previously stored in the memory. An identifier can be unique to a sheath or an identifier can be used for a number of sheaths. The identifier can identify the sheath as a particular type of sheath, such as a sheath that is reusable or a sheath that is not reusable. The identifier can be stored in the memory of the NFC tag by a manufacturer.

Figure 12:
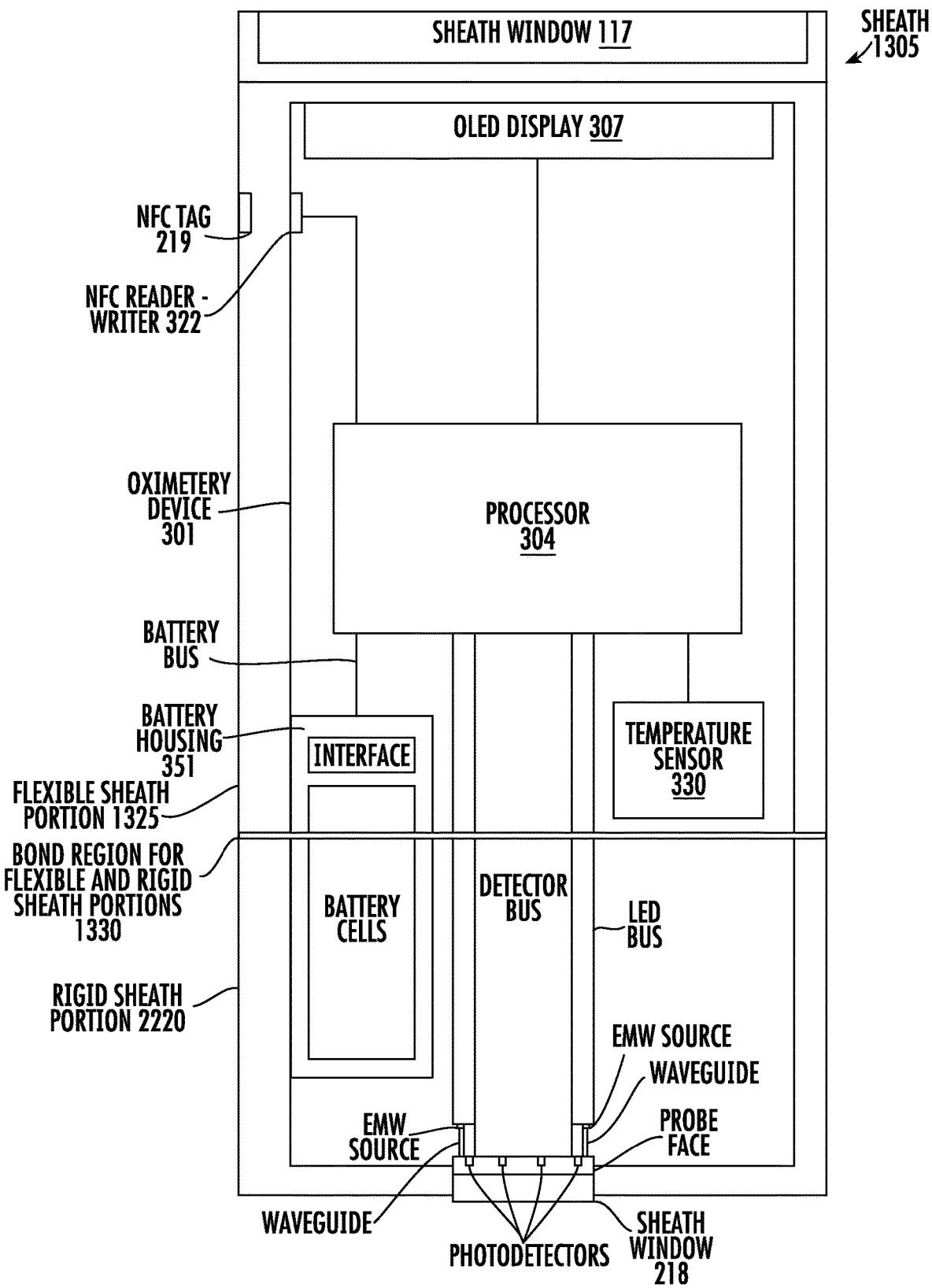
FIG. 12 is a block diagram of the system unit in the sheath, in an implementation.

FIG. 12 is a block diagram of system unit 301 in sheath 1305, in an implementation. Sheath 1205 is similar to sheath 205 but differs in that a lower body portion 1320 of the sheath is a relatively rigid plastic material and an upper body portion 1325 of the sheath is a relatively flexible plastic material. That is, the material of the upper body portion has a higher flexibility than the lower body portion. The upper and lower body portions may be coupled by an adhesive 1330, sonic welding, or another bonding material that forms a seal between the body portions. The seal is a barrier to patient tissue, patient liquid, and other contaminants. A top portion of the upper body portion can be seal so that a system unit can be sealed in the sheath where patient tissue, patient liquid, and other contaminants cannot reach the system unit when the unit is sealed in the sheath.

Figure 13:
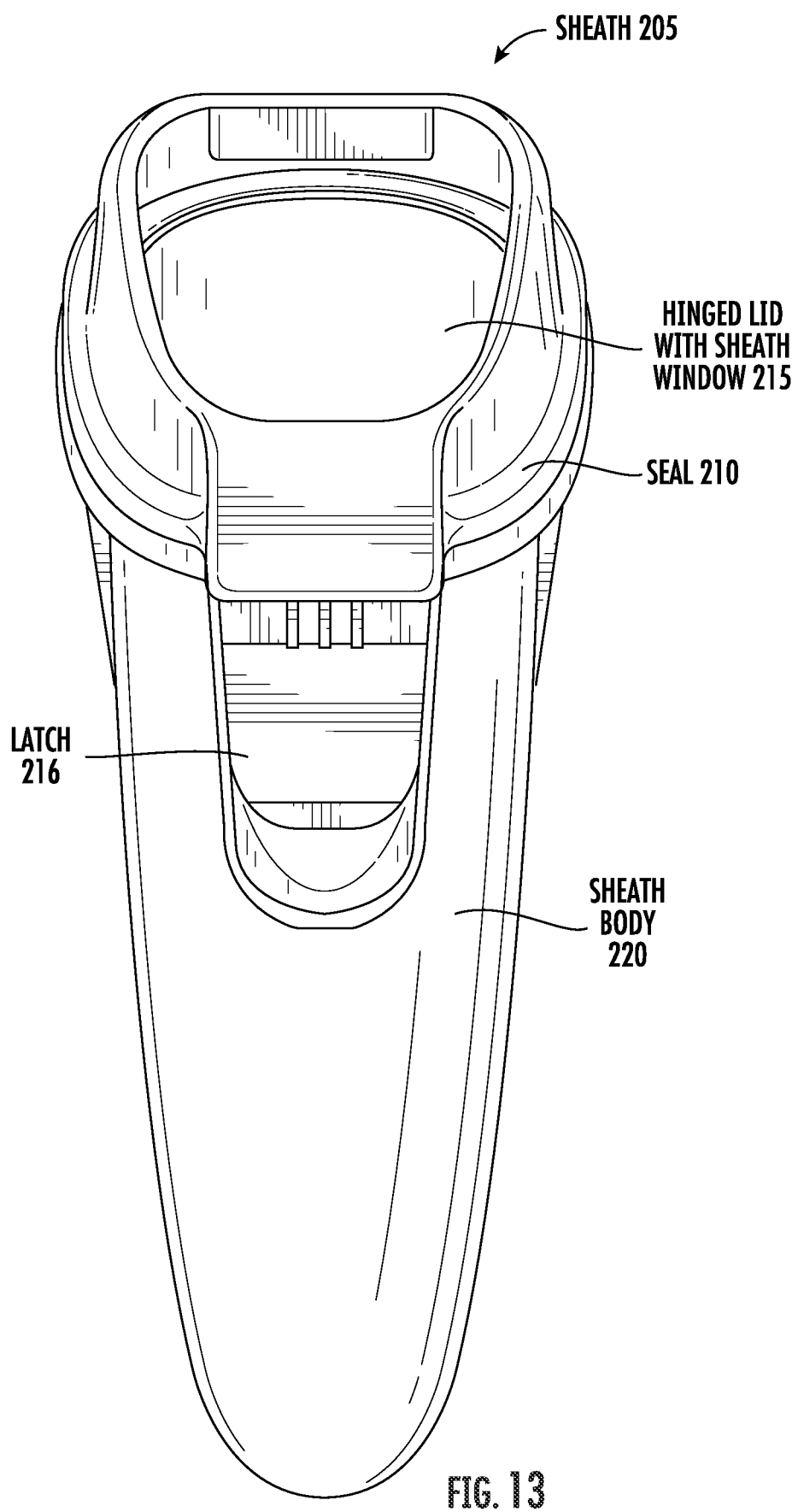
FIG. 13 shows a front view of the sheath, in an implementation.

FIG. 13 shows a front view of the sheath 205, in an implementation. The sheath is shown in FIG. 13 with the lid 215 closed against the body 220 of the sheath with the latch in a latched position against the body. The lid may be formed of a first plastic material that can be transparent (e.g., the window of the lid), translucent (e.g., portions of the lid attached to the window), opaque, or any combination of these properties. The body may be formed of a second plastic that can be transparent, translucent, opaque, or any combination of these properties. The second window of the body may be attached to the body via an adhesive (e.g., epoxy), plastic weld, or other fasteners. The second window may form a seal with the body where the second window attaches to the body where contaminants cannot pass through the seal to contaminate a system unit in the sheath via the seal.

In an implementation, the lid of the sheath is a plastic material. The material can be polycarbonate, acrylic, polyethylene terephthalate (PET), PETG, polyester, acrylonitrile butadiene styrene (ABS), or other plastic material. Polycarbonate, for example, is a material the lid may be made of because the material is easy to form, can be transparent, and can be sterilized by a variety of sterilization techniques and material, such as ethylene oxide (EtO), exposed to irradiation (both gamma and electron-beam), and steam autoclaving, isopropyl alcohol exposure, and other techniques and materials.

The body of the sheath is a plastic material. The material can be polycarbonate, acrylic, polyethylene terephthalate (PET), PETG, polyester, acrylonitrile butadiene styrene (ABS), or other plastic material. ABS, for example, is a material the body may be made of because the material is easy to form, and can be sterilized by a variety of sterilization techniques and material, such as ethylene oxide (EtO), exposed to irradiation (both gamma and electron-beam), and steam autoclaving, isopropyl alcohol exposure, and other techniques and materials.

The second window of the sheath at the bottom of the sheath is a plastic material or a glass material. In an implementation, the window is a plastic material. The material can be polycarbonate, acrylic, polyethylene terephthalate (PET), PETG, clear polyester, clear acrylonitrile butadiene styrene (ABS), or other transparent plastic material. PET, for example, is a material the second window may be made of because the material is easy to form, can be made optically flat, can be transparent, can be relatively strong while really thin, and can be sterilized by a variety of sterilization techniques and material, such as ethylene oxide (EtO), exposed to irradiation (both gamma and electron-beam), and steam autoclaving, isopropyl alcohol exposure, and other techniques and materials. The glass can be silica, borosilicate glass, optical glass, or other types of glass, such as other types of hard glass.

Figure 14:
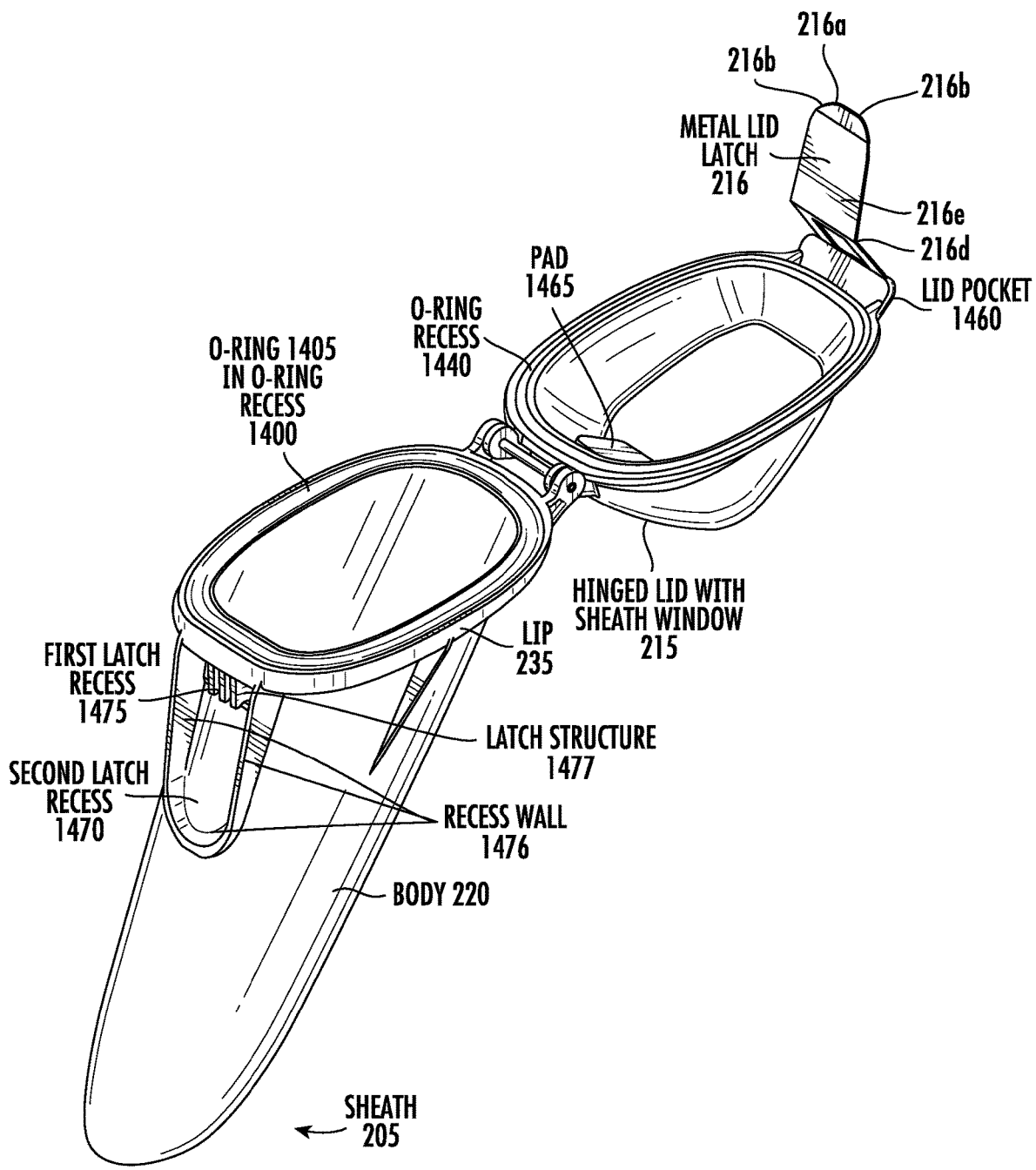
FIG. 14 shows a perspective view of the sheath, in an implementation.

FIG. 14 shows a perspective view of the sheath 205, in an implementation. The lid 215 is shown in an open position with respect to the body 220 where a system unit can be inserted into the sheath or removed from the sheath. The hinge that connects the lid and the body can be on a backside of the sheath. The body can include an O-ring recess 1400 of the top of the body. An O-ring 1405 is shown in the recess. The lid can also include an O-ring recess 4110 on the bottom of the lid. The O-ring recesses of the body and lid can contact the O-ring when the lid is closed against the body. The O-ring can form a seal that seals the lib to the body so that contaminants cannot enter the seal between the lid and body.

The latch can have a rounded end 216a and rounded corners 216b at the end of the latch. The end, corners, and edges of the latch can be relatively smooth. The smooth surface will not tear surgical gloves when the sheath and system unit are used.

Figure 15:
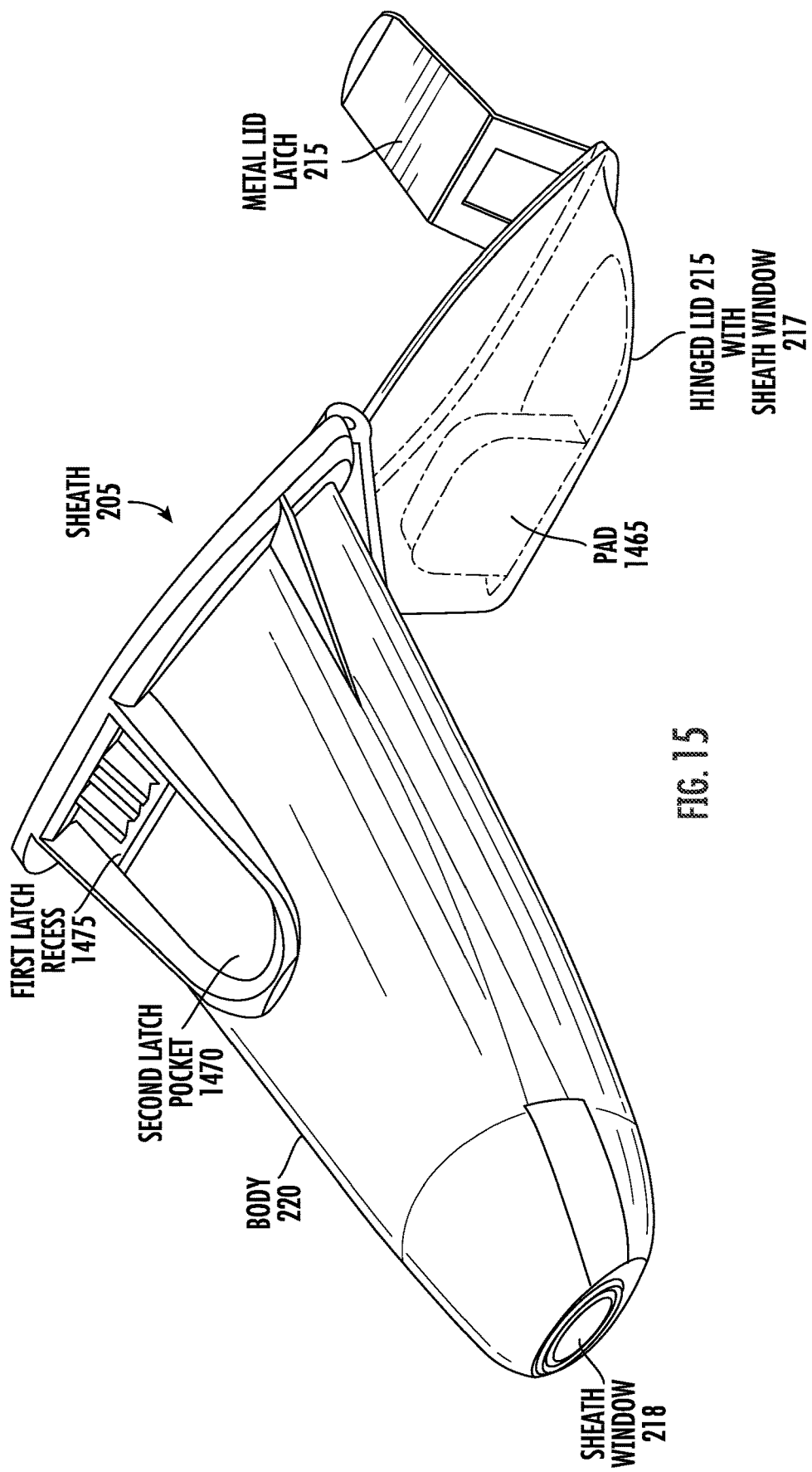
FIG. 15 shows a perspective view of the latch, in an implementation.

FIG. 15 shows a perspective view of the sheath 205, in an implementation. The lid is shown in an open position with respect to the body where a system unit can be inserted into the sheath or removed from the sheath. The figure shows the second sheath window 218 at the bottom of the body of the sheath. The second sheath window may generally be round from an end view. In a specific implementation, the second sheath window is circular. The upper and lower surface of the second sheath window may be approximately parallel.

Figure 16:
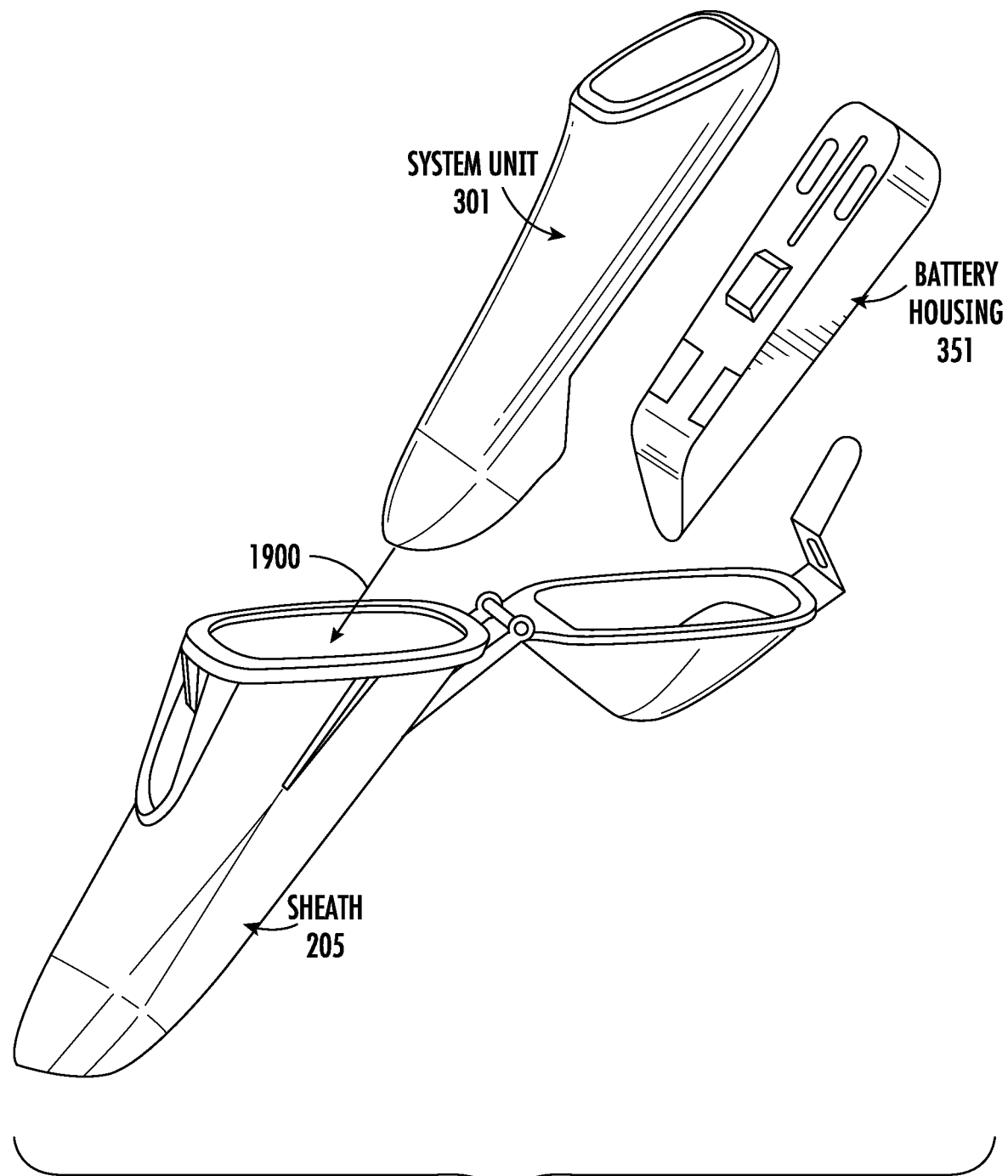
FIG. 16 shows a cross-sectional view of an upper portion of the sheath and shows a view between the lid and body where the O-ring is recessed the O-ring recess of the body of the sheath, in an implementation.

FIG. 16 shows a perspective view of the sheath, system unit, and power block, in an implementation. The sheath is shown with the sheath lid open and the system unit above the opening of the body of the sheath. When the power block is placed onto the system unit, the system unit and power block may be placed into the sheath as indicated by arrow 1900. The lid may then be closed and the system unit and power block sealed in the sheath ready for use.

Figure 17:
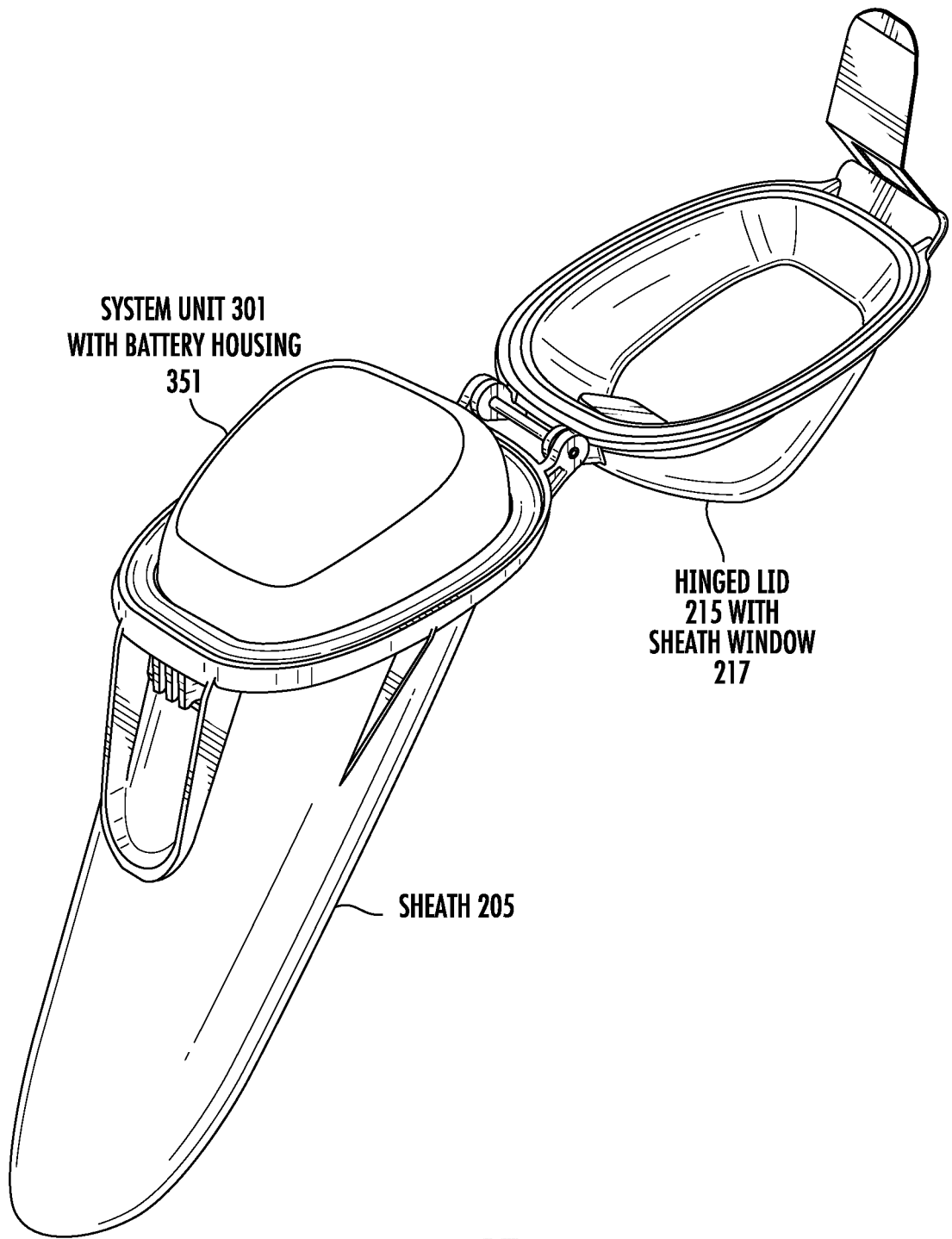
FIG. 17 shows a perspective view of the sheath, in an implementation.

FIG. 17 shows a perspective view of the sheath, system unit, and power block, in an implementation. The sheath is shown with the sheath lid open, the latch unlatched, and the system unit with the power block attached is in the sheath. The O-ring 1405 is shown positioned in the O-ring recess 1400. When the lid is closed, the O-ring is pinched in the O-ring recess by the top and bottom ridges 1420 and 1425. The display of the system unit is outside of the body of the sheath as shown when the lid is open when the probe face of the probe tip of the system unit contacts the second window of the sheath.

Figure 18:
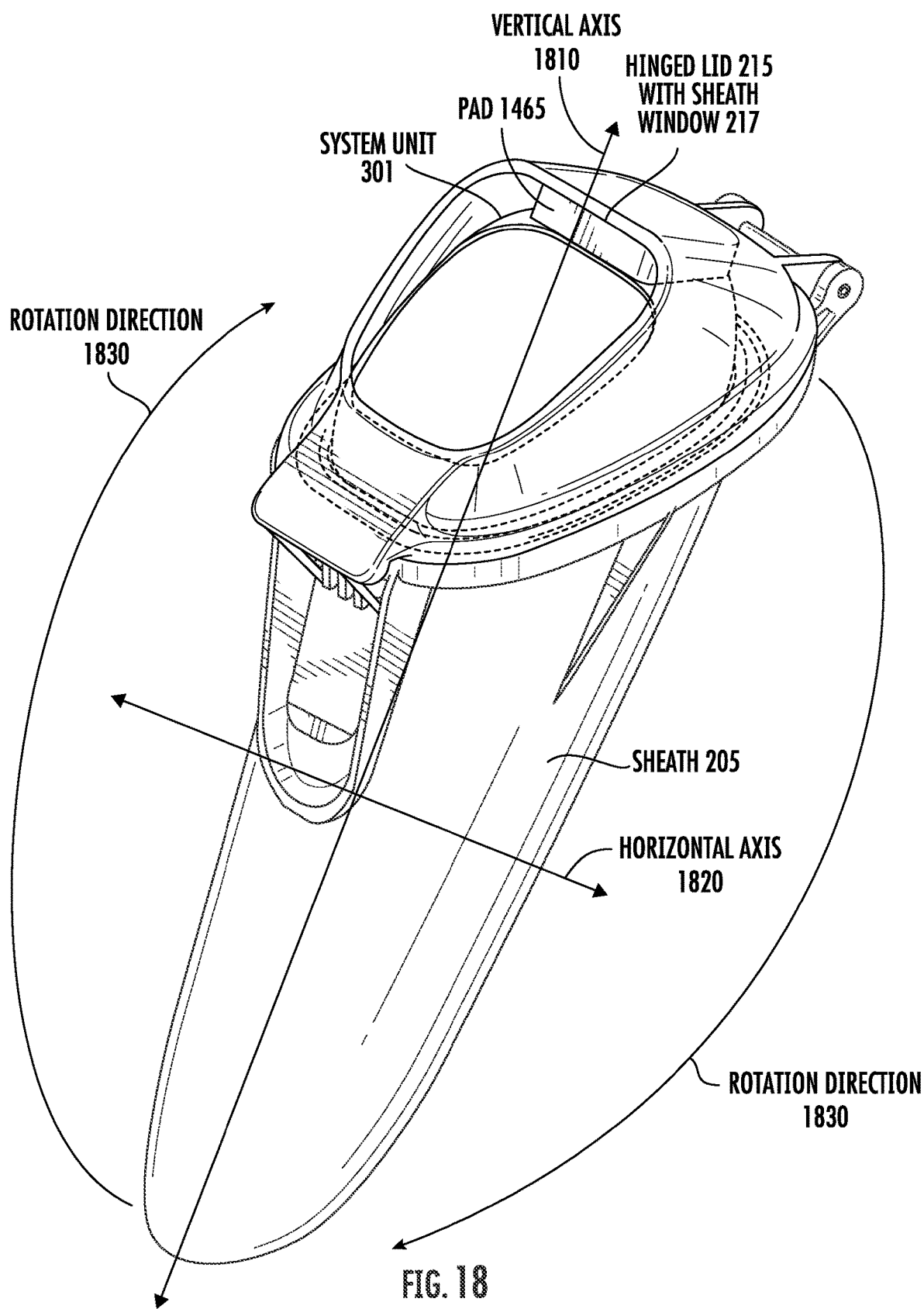
FIG. 18 shows a perspective view of the sheath, system unit, and power block, in an implementation.
Figure 19:
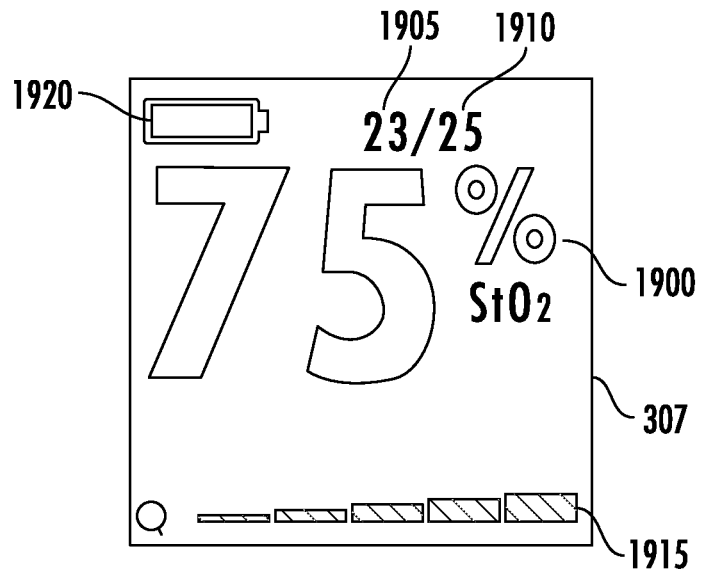
FIGS. 19-22 show oximetry information displayed on the display of the system unit, in an implementation.

FIG. 18 shows a perspective view of the sheath, system unit, and power block, in an implementation. The sheath is shown with the sheath lid closed, the latch latched, and the system unit with the power block attached is in the sheath. The ridges of the lid and body contact and pinch the O-ring to seal the system unit in the sheath. The display of the system unit is visible through the first window of the lid of the sheath. Information (e.g., text, graphics, or both) that is displayed on the display of the system unit is visible to a user looking through the second window of the lid. The display and window are both proximally located with the probe face and second window distally located when the system is ready for use. With the second window in contact with tissue, the display faces away from the tissue so that the display, through the first window, can be seen by a user.

FIGS. 19-22 show the display 307 of the system unit 301, in an implementation.

The display can display a number of pieces of information generated by the system unit. For example, the display can display oximetry information 1900, a number of permitted uses 1905 of the system unit that remain and a number of uses 1910 of the system unit that are available for a new unused system unit, a quality metric 1915, an indicator 1920 for an amount of available battery power in the battery, and a use message 1925. The oximetry information 1900 may include one or more of an oxygen saturation value (i.e., StO2), an oxygenated hemoglobin percentage (i.e., a saturated hemoglobin percentage), a deoxygenated hemoglobin percentage (i.e., an unsaturated hemoglobin percentage), an absorption coefficient, or other measured values. The total number of uses of the system unit may be from 5 to 100. In a specific implementation, the total number of uses of the system unit is 25. In the example shown in FIG. 19, the system unit has been used 2 times and 23 remaining uses are permitted by the system unit. The quality metric 1915 is a quality indicator for the displayed oximetry information 1900. The quality metric in the displayed embodiment is a bar graph. The battery power indicator 1920 may be a bar graph, a highlighted-dehighlighted graph, or other type of indicator. In the implementation shown in FIG. 19, the battery power indicator is a bar graph imposed with an image of a battery.

The use message (e.g., "lift up," "lift," or other message) may be a message for an action (e.g., lift the sheath or system unit if the system unit is used without a sheath) that a user may take so that the system unit will generate an average for a number of oximetry values that are generated by the system unit. The oximetry values can be any of the examples of the oximetry information 2100 described above, such as an oxygen saturation value. The average can be for a single tissue location of a patient or a number of tissue locations for the patient.

After the system unit has taken a first oximetry measurement and displays a first oximetry information 1900 on the display, the system unit may then display the use message. The use message may indicate that the user should "lift up" the system unit so that the second window 218 of the sheath or the probe face of the probe tip 108 of the system unit is not in contact with the tissue being measured. The probe face of the probe tip of the system unit may be in contact with the patient tissue if the system unit is used without the sheath.

Figure 20:
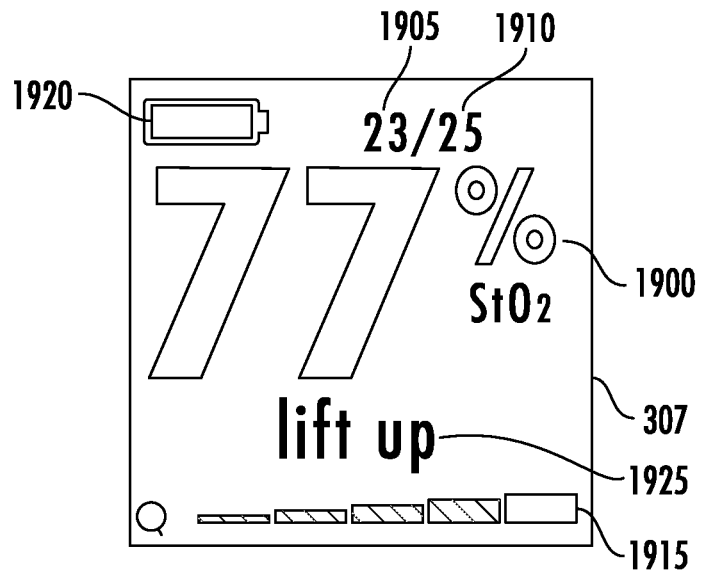

Referring to FIG. 20, after the system unit is lifted by the user and the second window or the probe face is not in contact with the tissue, the display may stop displaying oximetry information 1900 and display two bars 1903 or other information, such as another icon. When the bars are displayed the user can place the second window of the sheath or the probe face of the system unit back into contact with the tissue. The location on the tissue that the second window or probe face is placed in contact with can be the same tissue location that the system unit was lifted from or can be a different location. The system unit will thereafter generate second oximetry information (e.g., second oxygen saturation information for the tissue) for the second placement of the sheath, system unit, or both.

The display of the system unit may continue to display the two bars 1903 when the second oximetry information is generated or may display the second oximetry information (e.g., second oxygen saturation information). The system unit may also display that there is one average generated 1930 for the first and second oximetry information (e.g., "Avg 1: —%") for the first and second placements on the tissue. In an implementation, for the tissue location, the system unit does not display an average value, but displays other information, such as an icon (e.g., two bars). In an implementation, the first oximetry information for a first tissue location is displayed on the display in the location where averages are displayed, it being understood that a single oximetry measurement for a single tissue location is not an average for a number of tissue locations (e.g., greater than two tissue locations).

After the second oximetry information is generated, the display may again display the use message (e.g., "lift up"). Thereafter the process of lifting and placing the sheath, system unit, or both onto the tissue (e.g., at the same tissue location or a different tissue location) may be repeated. Thereafter, the system unit may generate third oximetry information for the tissue on which the second window or probe face is placed. In an implementation, the system unit displays an average value when a third average value of the oximetry information is generated. That is, the average of the first, second, and third oximetry information is referred to as the third average value. In other implementations, the system unit displays an average value when a second average value of oximetry information is generated or a higher number of average values of the oximetry information is generated.

Figure 21:
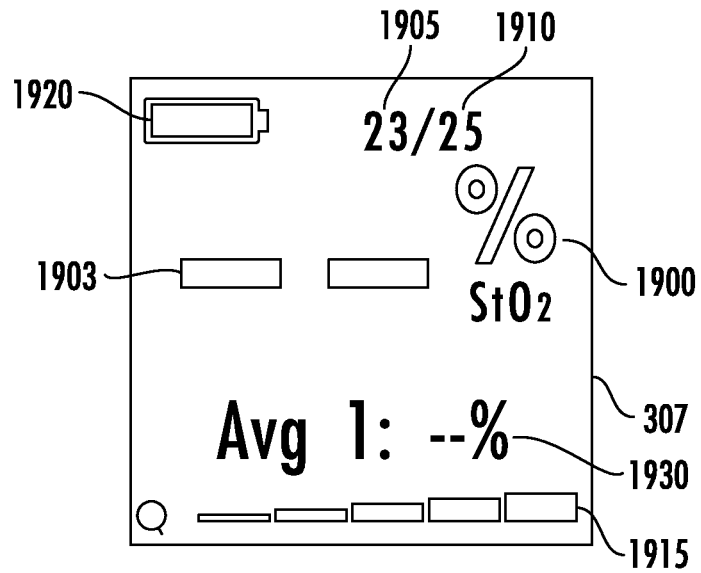

Referring to FIG. 21, the third average value for the oximetry information is displayed on the display. After the third oximetry information is generated, the use message may be displayed for each subsequent oximetry information generated (e.g., fourth, fifth, sixth, seventh, or more) and an average may be generated and displayed.

In an implementation, the average is no longer accumulated after nine averages are generated. In an implementation, the average is reset if the accelerometer detects that the system unit is turned upside down (i.e., inverted). That is, if the system unit is rotated vertically by about 180 degrees+/− about 45 degrees the average will be reset.

Figure 23:
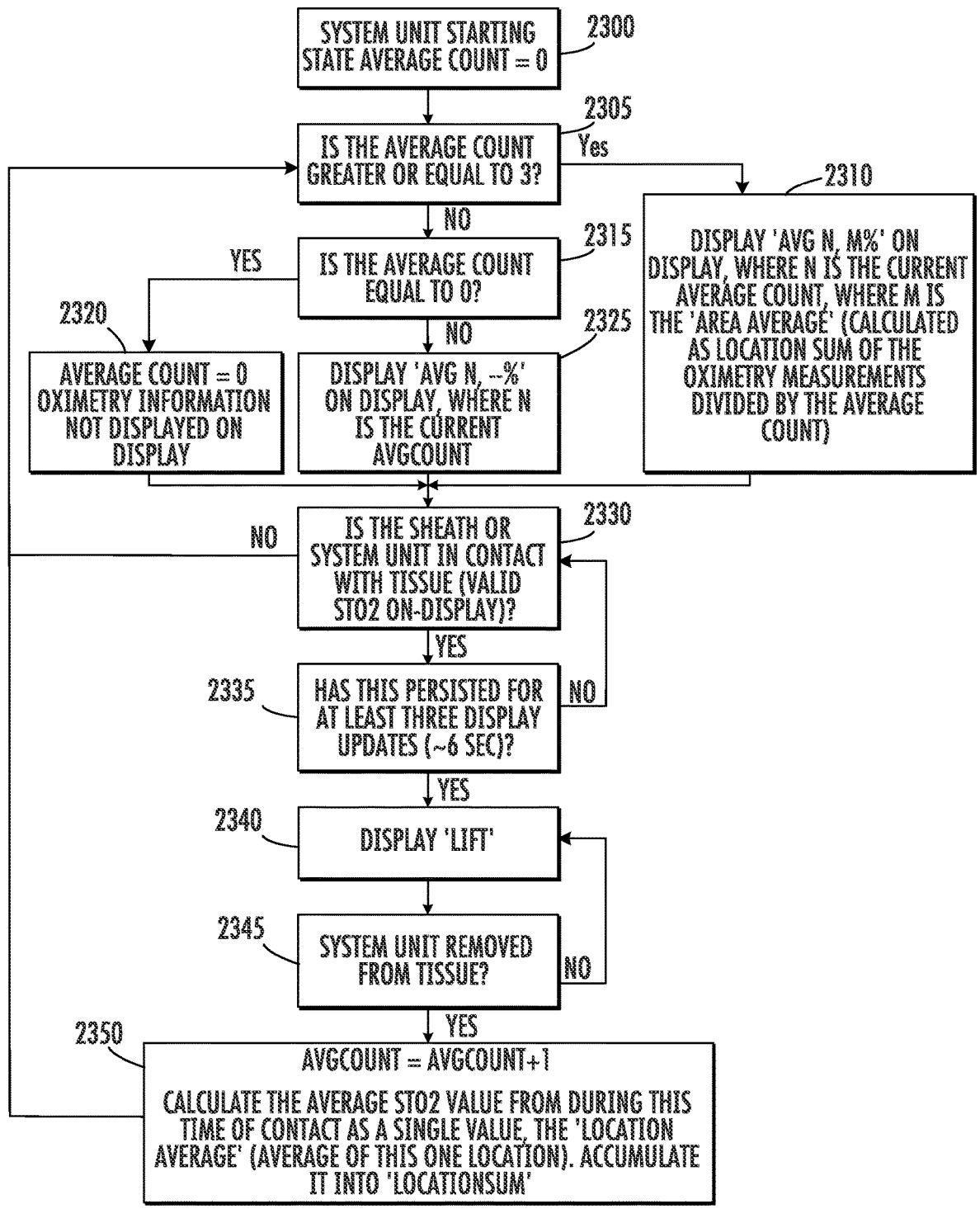
FIG. 23 is a flow diagram of a method of operation of the system unit for generating average oximetry information, in an implementation.

FIG. 23 is a flow diagram of a method of operation of the system unit for generating average oximetry information, in an implementation. The flow diagram shows an example embodiment in an implementation. Steps may be added, removed, or combined without deviating from the method.

At 2300, at an initial state of the method, no oximetry measurements (i.e., "average count") have been made for tissue to be measured of a single patient. For each tissue location that oximetry measurements are made, the average count may be incremented by one if a set of lift and place rules of the system unit are satisfied or may remain unchanged if the set lift and place rules are not satisfied. For example, if the set of rules are satisfied for a first tissue location, then the average count is one. If the set of rules are satisfied for a second tissue location, then the average count is incremented by one and is two. If the set of rules are satisfied for a third tissue location, then the average count is incremented by one and is three. If the set of rules are satisfied for a fourth tissue location, then the average count is incremented by one and is four. If the set of rules are satisfied for a fifth tissue location, then the average count is incremented by one and is five. If the set of rules are satisfied for a sixth tissue location, then the average count is incremented by one and is six. This process of incrementing the average count continues to increment by one for each subsequent tissue location that the system unit is placed at if the set of rules is satisfied.

If the lift and place rules are not satisfied, for example, for the third tissue location, then the average count is not incremented by one, and the average count may remain at two. The lift and placement rules used by the system unit to increment the average count or not increment the average count are described with respect to the following steps of the method.

In an embodiment, the values for the average count are stored in a memory (e.g., a buffer memory) of the system. The stored value for the average count is incremented when the lift and place set of rules are satisfied for tissue oximetry measurements for the tissue locations of the patient tissue of the select patient.

At 2305, the system unit interrogates the memory (e.g., the buffer memory) of the system unit to determine whether the average count is greater than or equal to three. If the average count is greater than or equal to three, then oximetry measurements have been made for three tissue location of the patient tissue and the lift and place rules have been satisfied for the measurements made by the system unit. If the average count is less than three, then oximetry measurements have not been made for three tissue locations of the patient tissue and, lift and place rules have been satisfied for the measurements made by the system unit, or both.

At 2305, if the average count is greater than or equal to three (e.g., interrogate the memory that stores the average count), then at 2310 the display of the system unit displays the current average count and average information for the oximetry measurements (e.g., average oxygen saturation measurements) for the tissue locations. More specifically, the system unit may display "Avg N, M %" (see FIG. 22) on the display, where N is the current average count and M is the average of the oximetry measurements. The average by the calculated as the sum of the oximetry measurements divided by the average count. In alternative implementations, the average is calculated by other techniques.

At 2305, if the average count is less than three, then at 2315, the system unit determines whether the average count is equal to zero.

At 2315, if the average count is zero, then at 2320, the system unit does not display oximetry information on the display.

At 2315, if the average count is greater than zero, then at 2325, the system unit displays the current average count and no average information for the oximetry measurements. For example, the system unit may display "Avg N, —%" (see FIG. 21) on the display, where N is the average count and the dashes indicate that no average information for the oximetry information is displayed. The display may display the two dashes or other text or another icon to indicate that no average for the oximetry measurement is displayed.

At 2330, the system unit makes one or more oximetry measurements for a tissue location. If the system unit is executing the method for a first time, the tissue location is a first tissue location. If the system unit is executing the method for a second time, the tissue location may be a second tissue location. If the system unit is executing the method for a third time, the tissue location may be a third tissue location. The tissue locations increase as the method continues to be executed (loop through the loop portions of the method). The system unit determines whether the sheath or system unit (e.g., system unit used without the sheath) contacts the tissue and whether the oximetry information (e.g., oxygen saturation information) for the oximetry measurement is valid oximetry information. The system unit will display the oximetry information if the oximetry information is valid oximetry information.

At 2330, if the sheath or system unit is not in contact with the tissue, if the oximetry information is not valid, or both, then the method return to step 2305 and repeats the described steps until the method is terminated, such as by inversion of the system unit described below with respect to FIGS. 28 and 29.

At 2330, if the sheath or system unit is in contact with the tissue, if the oximetry information is valid, or both, then at 2335 the system unit determines whether this state (e.g., if the sheath or system unit is in contact with the tissue, if the oximetry information is valid, or both) has persisted for at least three display update cycles. The display may update the oximetry information that is displayed on the display after one update cycle that has a threshold cycle time. The threshold cycle time may be from about 1 second to about 3 seconds, from about 2 second and 4 seconds, or another duration. In an implementation, the threshold cycle time is from about 2 seconds to 2.3 second. Thus, three update cycle times may be from about 3 seconds to about 9 seconds, about 6 second to about 12 seconds, or another duration. In the specific embodiment, three update cycles may be about 6 seconds.

At 2335, if the state (e.g., if the sheath or system unit is in contact with the tissue, if the oximetry information is valid, or both) has not persisted for at least three display update cycles, then the system unit continues to make oximetry measurements for the tissue location at 2330.

At 2340, if the state (e.g., if the sheath or system unit is in contact with the tissue, if the oximetry information is valid, or both) has persisted for at least three display update cycles, then the system unit display a use message (e.g., a "lift up" message) on the display at 2340. The use message informs the user that the user has to take a specific action with the system unit so that the system unit can accumulate an average of oximetry measurements.

At 2345, the system unit determines whether the sheath or system unit has been lifted, such as if the system unit has been lifted out of contact with the tissue.

In an implementation, the lift is detected by determining that measured oximetry information is no longer valid for the patient tissue. Invalid oximetry information may be outside of a range of predetermined valid oximetry information. Invalid oximetry information may include an oxygen saturation measurement that provides an invalid result, for example, from extreme property predictions, a poor fit of measured values to a lookup database of stored Monte Carlo simulated reflectance curves, ambient light saturation (e.g., when the system unit is lifted from tissue, or other factors.

When the system unit detects that a lift has occurred, the system unit determines whether the lift occurred when the lift up message was displayed on the display. The system unit may store oximetry information in a memory location in which the average oximetry information is stored. The system unit may also store information (e.g., the average count) for the number of times oximetry information is stored for the average oximetry information.

At 2345, if the system unit has not been removed from the tissue, has been removed from the tissue when the use message is not displayed, or both, then the lift message is displayed at 2340.

At 2345, if the system unit has been removed from the tissue, has been removed from the tissue when the use message is displayed, or both, then at 2350 the average count is incremented by one. The average for the oximetry information (e.g., oxygen saturation value) is generated for the tissue locations. The incremented average count and the average oximetry information is displayed on the display. Thereafter, the flow of the method repeats at 2305.

Table A below shows information that is used by the system unit to generate an average for oximetry information, in an implementation. The table shows a number of oximetry measurements that may be made when the sheath or system unit is placed in contact with various locations on a patient's tissue. The values of Table A may be generated according to the method described above with respect to FIG. 23 and alternatives of FIG. 23 also described above.

The first column in the table, labeled "Number of measurements included in an average," shows the number of times the sheath or system unit has been removed from the tissue while the user message (e.g., "lift up") is displayed on the display. For example, the number 1 entry in the first column of the table may be for an initial lift up of the sheath or system unit for a first tissue location for a new average. The number 2 entry in the first column of the table may be for a lift up of the sheath or system unit from a second tissue location when the sheath or system unit has been lifted from the first tissue location and lifted from the second tissue location. The number 3 entry in the first column of the table may be for a third lift up of the sheath or system unit from a third tissue location when the sheath or system unit has been lifted from the second tissue location and lifted from the third tissue location. The number 4 entry in the first column of the table may be for a fourth lift up of the sheath or system unit from a fourth tissue location when the sheath or system unit has been lifted from the third tissue location and lifted from the fourth tissue location.

The second column in the table, labeled "Oximentry measurements during a placement of the sheath and system unit at a tissue location," shows a number of pieces of oximetry information (e.g., oxygen saturation values) that are generated when the sheath or system unit is placed at a location on a patient's tissue. For example, the first row of oximetry information of the second column shows six values (e.g., 27, 50, 74, 66, 79, 72) for oximetry information generated by the system unit for the first tissue location. The second row of oximetry information of the second column shows four values (e.g., 62, 71, 77, 68) for oximetry information generated by the system unit for the second tissue location. The second tissue location is the location that the second window of the sheath or the probe face of the system unit is placed after being lifted from the first tissue location. The third row of oximetry information of the second column shows five values (e.g., 0, 0, 64, 73, 70) for oximetry information generated by the system unit for the third tissue location. The third tissue location is the location that the second window of the sheath or the probe face of the system unit is placed after being lifted from the second tissue location. The fourth row of oximetry information of the second column shows four values (e.g., 0, 0, 64, 73, 70) for oximetry information generated by the system unit for the fourth tissue location. The fourth tissue location is the location that the second window of the sheath or the probe face of the system unit is placed after being lifted from the third tissue location.

The last piece of oximetry information generated for each of the tissue locations is used by the system unit to generate an average of the oximetry information. For example, the third column, labeled "Measurements used for average," of the table shows the measurements that are used for generating an average. The first data row of the third column includes the value 72 for the oximetry information. This value is the last piece of oximetry information (e.g., 72) generated by the system unit for the first tissue location, which is shown in the second column of the table.

The second data row of the third column includes the value 68 for the oximetry information. This value is the last piece of oximetry information (e.g., 68) generated by the system unit for the second tissue location, which is shown in the second column of the table.

The third data row of the third column includes the value 70 for the oximetry information. This value is the last piece of oximetry information (e.g., 70) generated by the system unit for the third tissue location, which is shown in the second column of the table. The fourth data row of the third column includes the value 74 for the oximetry information. This value is the last piece of oximetry information (e.g., 74) generated by the system unit for the fourth tissue location, which is shown in the second column of the table.

The fourth column in the table shows average values that may be displayed on the display of the system unit. In an implementation, an average value for the first and second tissue locations is not shown on the display. In an implementation, an average value for the first tissue location is not shown on the display while an average for a second or higher number of tissue locations is displayed on the display. As described above, the display may display dashed lines or another icon for the average value for the first and second tissue locations. When the average values are generated for the third tissue location or higher number tissue location, these average values may be displayed on the display.

TABLE A

| Number of measurements included in an average | Oximetry measurements during a placement of the sheath and system unit at a tissue location | Measurements used for average | Average |
| --- | --- | --- | --- |
| 1 | 27, 50, 74, 66, 79, 72 | 72 | — |
| 2 | 62, 71, 77, 68 | 68 | — |
| 3 | 0, 0, 64, 73, 70 | 70 | 70 |
| 4 | 55, 0, 20, 74 | 74 | 71 |

In an implementation, the system unit stores the values in two or more of the columns. The system unit may also store a sum of each of the measurements used for the average show in column three. For example, after the measurements of the first tissue location are made, the system unit may store the value 72. After the measurements for the first and second tissue locations are made, the system unit may store the sum (e.g., 140) of the first and second values (e.g., 72 and 68) of the third column. After the measurements for the first, second, and third tissue locations are made, the system unit may store the sum (e.g., 210) of the first, second, and third values (e.g., 72, 68, and 70) of the third column. After the measurements for the first, second, third, and fourth tissue locations are made, the system unit may store the sum (e.g., 284) of the first, second, and third values (e.g., 72, 68, 70, and 74) of the third column. Fewer values may be included in the stored sum if the use message (e.g., "lift up") is not displayed when the sheath or system unit is lifted from the tissue as described above with respect to FIG. 23.

In an implementation, an average can be reset and a new average can be initiated when the system unit is rotated through one or more predetermined angles and about a predetermined axis. For the reset to occur, the system unit can be vertically rotated where the display of the system unit is rotated down as the probe face of the system unit is rotated up. That is, the system unit can be rotated vertically as indicated by arrows 1830 in FIG. 18. The rotation can be about any horizontal axis 1820 that is perpendicular to vertical axis 1810. Vertical axis can 1810 extends through the probe face of the system unit and the display of the system unit.

Figure 29:
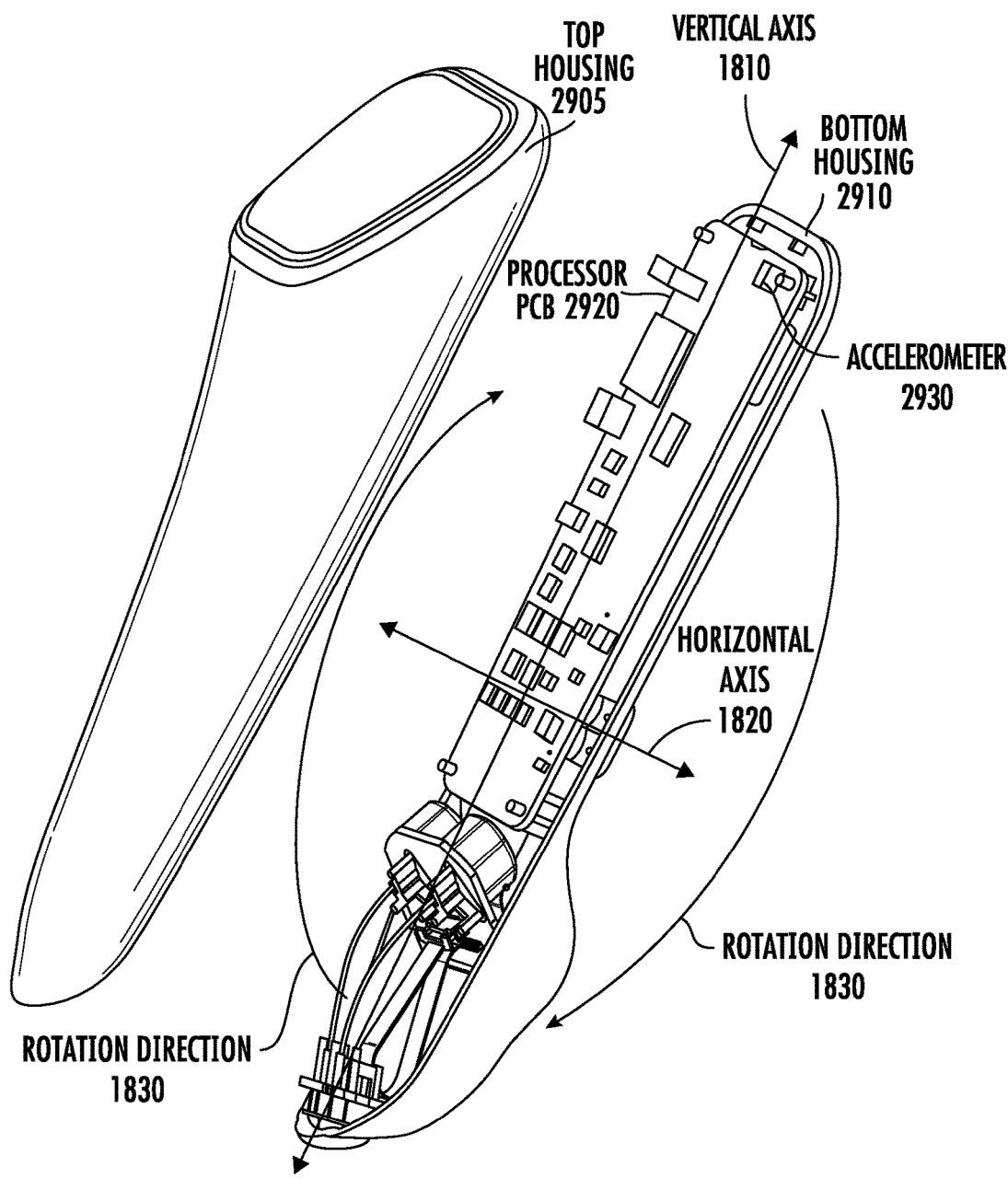
FIG. 29 shows the system unit with the top housing separated from the bottom housing.

FIG. 29 shows the system unit with the top housing 2905 separated from the bottom housing 2910. In an embodiment, the vertical axis 1810 is parallel to a surface of a printed circuit board (PCB) 2920 that is located in the system unit. The surface of the PCB is the surface on which the accelerometer circuit 2930 and other circuits of the system unit are mounted. The PCB is approximately parallel to a back surface of the bottom housing which the PCB is mounted on.

An average can be reset when the average number is reset (e.g., reset to zero in memory) to zero. New oximetry measurement information for one or more tissue locations can be stored in the memory for a new average. In an implementation, the memory storing the average information can be reset.

For the reset to occur the system unit can be rotated through a first angle downward (e.g., the display is rotated down and the probe face is rotated up). Thereafter, the system unit can rotated through a second angle upward (e.g., the display is rotated up and the probe face is rotated down). The first and second angles can be different angles to that the reset occurs according to a hysteresis process. That it, a reset can occur after the downward rotation, but a second reset will not occur after the subsequent upward rotation.

Figure 28:
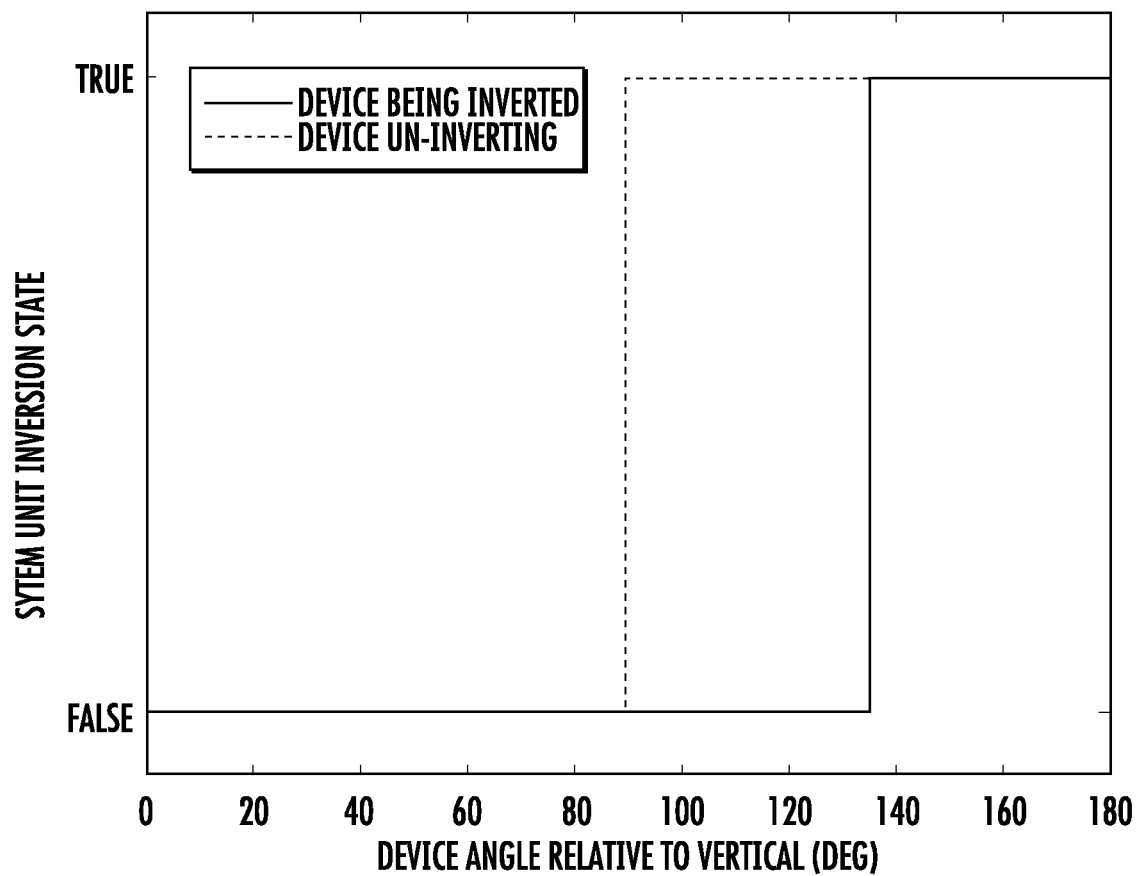
FIG. 28 is a graph showing the first rotation angle and the second rotation angle that the system unit may be vertically rotated by to affect the average reset.

FIG. 28 is a graph showing the first rotation angle and the second rotation angle that the system unit may be vertically rotated by to affect the average reset. The first angle is represented by the solid line in the graph and identified in the graph's legend as "Device being inverted," (e.g., the display is rotated down and the probe face is rotated up). The system unit being inverted is sometimes referred to as the system unit being "dipped." The first angle may be from about 130 degrees to about 150 degrees. In an embodiment, the first angle is 135 degrees. The second angle is represented by the dashed line in the graph and identified in the graph's legend as "Device being un-inverting," (e.g., the display is rotated up and the probe face is rotated down). The accelerometer of the system unit may be configured to detect vertical rotations. The accelerometer may not be configured to determine whether the device is oriented upright (e.g., display of the system unit oriented up and the probe face oriented down) or oriented down (e.g., display of the system unit oriented down and the probe face oriented up). By configuring the system to detect the system unit being rotated down at the first angle and being rotated up at the second angle, the system unit can use motion detection detected by the accelerometer and the hysteresis to determine whether the system unit is being rotated up or rotated down.

Figure 24:
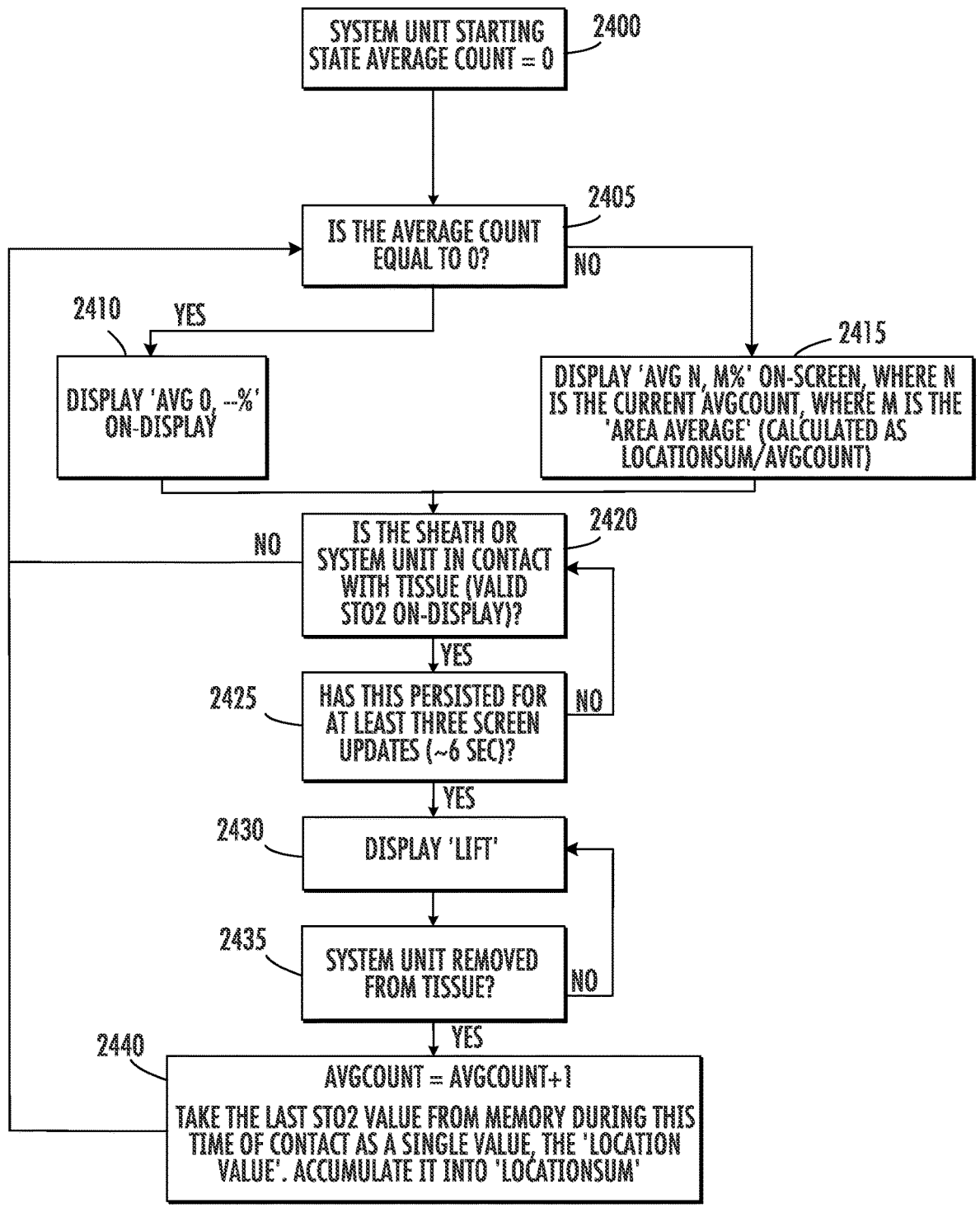
FIG. 24 is a flow diagram of a method of operation of the system unit for generating average oximetry information, in an implementation.

FIG. 24 is a flow diagram of a method of operation of the system unit for generating average oximetry information, in an implementation. The flow diagram shows an example embodiment in an implementation. Steps may be added, removed, or combined without deviating from the method.

At 2400, at an initial state of the method, no oximetry measurements (i.e., "average count") have been made for tissue to be measured of a single patient. For each tissue location that oximetry measurements are made, the average count may be incremented by one if a set of lift and place rules of the system unit are satisfied or may remain unchanged if the set lift and place rules are not satisfied. For example, if the set of rules are satisfied for a first tissue location, then the average count is one. If the set of rules are satisfied for a second tissue location, then the average count is incremented by one and is two. If the set of rules are satisfied for a third tissue location, then the average count is incremented by one and is three. If the set of rules are satisfied for a fourth tissue location, then the average count is incremented by one and is four. If the set of rules are satisfied for a fifth tissue location, then the average count is incremented by one and is five. If the set of rules are satisfied for a sixth tissue location, then the average count is incremented by one and is six. This process of incrementing the average count continues to increment by one for each subsequent tissue location that the system unit is placed at if the set of rules is satisfied.

If the lift and place rules are not satisfied, for example, for the third tissue location, then the average count is not incremented by one, and the average count may remain at two. The lift and placement rules used by the system unit to increment the average count or not increment the average count are described with respect to the following steps of the method.

In an embodiment, the values for the average count are stored in a memory (e.g., a buffer memory) of the system. The stored value for the average count is incremented when the lift and place set of rules are satisfied for tissue oximetry measurements for the tissue locations of the patient tissue of the select patient.

At 2405, the system unit interrogates the memory (e.g., the buffer memory) of the system unit to determine whether the average count is greater than zero or equal to zero. If the average count is greater than zero, then an oximetry measurement has been made for at least one tissue location of the patient tissue and the lift and place rules have been satisfied for the measurements made by the system unit. If the average count is zero, then no oximetry measurements have been made.

At 2405, if the average count is greater than zero (e.g., interrogate the memory that stores the average count), then at 2410 the display of the system unit displays the current average count and average information for the oximetry measurements (e.g., average oxygen saturation measurements) for the tissue locations. More specifically, the system unit may display "Avg N, M %" (see FIG. 22) on the display, where N is the current average count and M is the average of the oximetry measurements, which are calculated as the sum of the oximetry measurements divided by the average count.

At 2405, if the average count is zero, then at 2415, the system unit displays the current average count and no average information for the oximetry measurements. For example, the system unit may display "Avg 0,--%" (see FIG.

21) on the display, where N is the average count and the dashes indicate that no average information for the oximetry information is displayed. The display may display the two dashes or other text or another icon to indicate that no average for the oximetry measurement is displayed.

At 2420, the system unit makes one or more oximetry measurements for a tissue location. If the system unit is executing the method for a first time, the tissue location is a first tissue location. If the system unit is executing the method for a second time, the tissue location may be a second tissue location. If the system unit is executing the method for a third time, the tissue location may be a third tissue location. The tissue locations increase as the method continues to be executed (loop through the loop portions of the method). The system unit determines whether the sheath or system unit (e.g., system unit used without the sheath) contacts the tissue and whether the oximetry information (e.g., oxygen saturation information) for the oximetry measurement is valid oximetry information. The system unit will display the oximetry information if the oximetry information is valid oximetry information.

At 2420, if the sheath or system unit is not in contact with the tissue, if the oximetry information is not valid, or both, then the method return to step 2405 and repeats the described steps until the method is terminated, such as by inversion of the system unit described above with respect to FIGS. 28 and 29.

At 2420, if the sheath or system unit is in contact with the tissue, if the oximetry information is valid, or both, then at 2425 the system unit determines whether this state (e.g., if the sheath or system unit is in contact with the tissue, if the oximetry information is valid, or both) has persisted for at least three display update cycles. The display may update the oximetry information that is displayed on the display after one update cycle that has a threshold cycle time. The threshold cycle time may be from about 1 second to about 3 seconds. In an implementation, the threshold cycle time is about 2 seconds. Thus, three update cycle times may be from about 3 seconds to about 9 seconds. In the specific embodiment, three update cycles may be about 6 seconds.

At 2425, if the state (e.g., if the sheath or system unit is in contact with the tissue, if the oximetry information is valid, or both) has not persisted for at least three display update cycles, then the system unit continues to make oximetry measurements for the tissue location at 2420.

At 2425, if the state (e.g., if the sheath or system unit is in contact with the tissue, if the oximetry information is valid, or both) has persisted for at least three display update cycles, then the system unit displays a use message (e.g., a "lift up" message) on the display at 2430. The use message informs the user that the user has to take a specific action with the system unit so that the system unit can accumulate an average of oximetry measurements.

At 2435, the system unit determines whether the sheath or system unit has been lifted, such as if the system unit has been lifted out of contact with the tissue.

In an implementation, the lift is detected by determining that measured oximetry information is no longer valid for the patient tissue. Invalid oximetry information may be outside of a range of predetermined valid oximetry information. Invalid oximetry information may include an oxygen saturation measurement that provides an invalid result, for example, from an extreme property prediction, a poor fit of measured values to a lookup database of stored Monte Carlo simulated reflectance curves, ambient light saturation (e.g., when the system unit is lifted from tissue, or other factors.

When the system unit detects that a lift has occurred, the system unit determines whether the lift occurred when the lift up message was displayed on the display. The system unit may store oximetry information in a memory location in which the average oximetry information is stored. The system unit may also store information (e.g., the average count) for the number of times oximetry information is stored for the average oximetry information.

At 2435, if the system unit has not been removed from the tissue, has been removed from the tissue when the use message is not displayed, or both, then the lift message is displayed at 2430.

At 2445, if the system unit has been removed from the tissue, has been removed from the tissue when the use message is displayed, or both, then at 2440 the average count is incremented by one. The average for the oximetry information (e.g., oxygen saturation value) is generated for the tissue locations. The incremented average count and the average oximetry information is displayed on the display. Thereafter, the flow of the method repeats at 2405.

Table B below shows information that is used by the system unit to generate an average for oximetry information, in an implementation. Similar to Table A above, Table B includes columns for the "Number of measurements included in an average," "Oximentry measurements during a placement of the sheath and system unit at a tissue location," "Measurements used for average," and "Average." Table B differs from Table A in that the average values shown in the fourth column are displayed on the display. The values of Table B may be generated according to the method described above with respect to FIG. 24 and alternatives of FIG. 24 also described above.

TABLE B

| Number of measurements included in an average | Oximetry measurements during a placement of the sheath and system unit at a tissue location | Measurements used for average | Average |
| --- | --- | --- | --- |
| 1 | 27, 50, 74, 66, 79, 72 | 72 | 72 |
| 2 | 62, 71, 77, 68 | 68 | 70 |
| 3 | 0, 0, 64, 73, 70 | 70 | 70 |
| 4 | 55, 0, 20, 74 | 74 | 71 |

Figure 25:
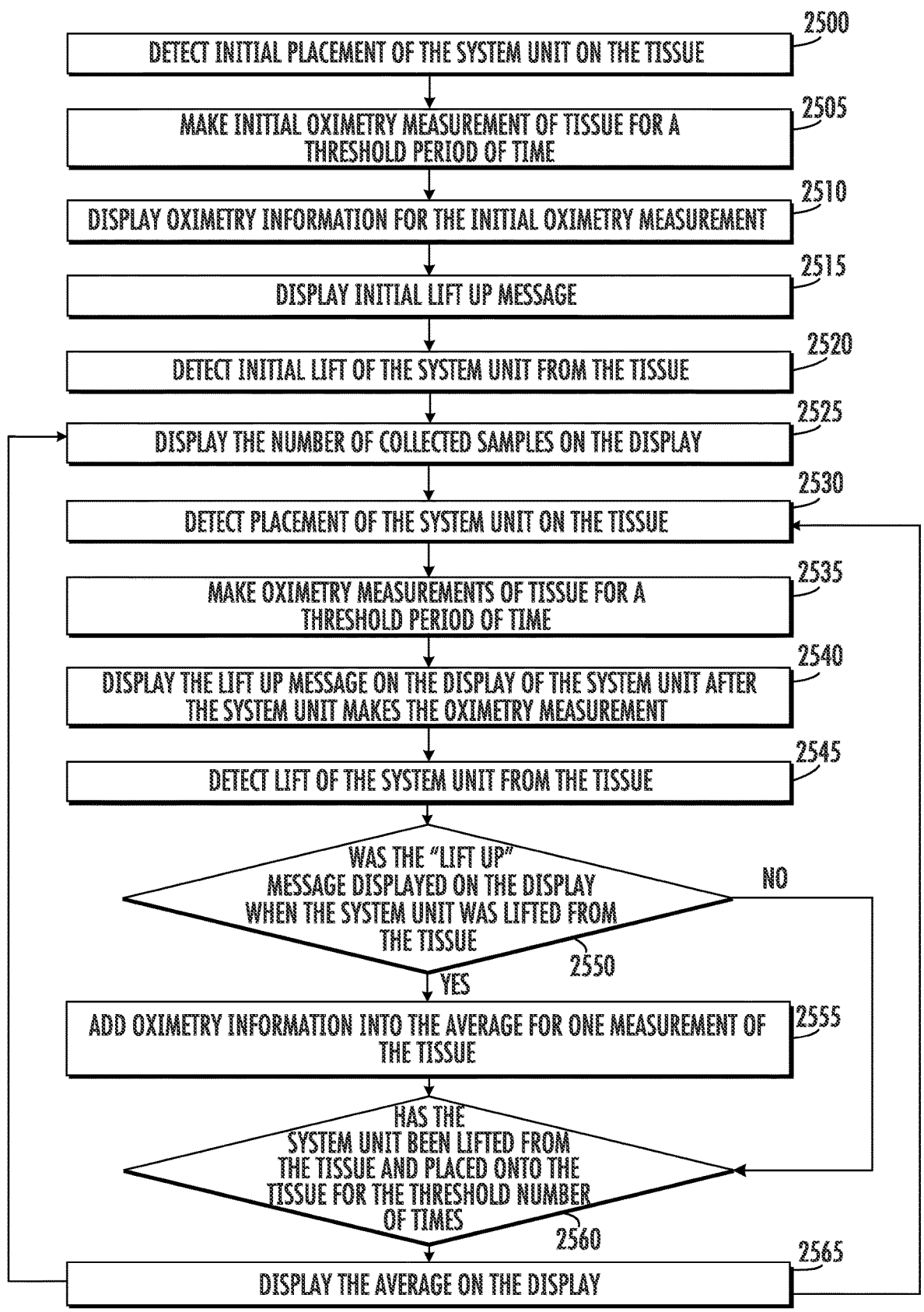
FIG. 25 is a flow diagram of a method of operation of the system unit for generating average oximetry information, in an implementation.

FIG. 25 is a flow diagram of a method of operation of the system unit for generating average oximetry information, in an implementation. The flow diagram shows an example embodiment in an implementation. Steps may be added, removed, or combined without deviating from the method.

At 2500, the second sheath window of the sheath or the probe face of the probe tip of the system unit (e.g., if used without the sheath) is initially placed into contact with patient tissue by a user at a first tissue location.

At 2505, the system unit makes a first oximetry measurement of the patient tissue and generates first oximetry information. The system unit may store the determined oximetry information in one of the memories of the system unit, such as the system unit RAM 312. This first oximetry information may be stored in a memory location in which the average oximetry information is stored.

At 2510, the display of the system unit displays the first oximetry information (e.g., oxygen saturation) that is determined by the system unit.

At 2515, after the first oximetry measurement is performed for a threshold period of time, the use message (e.g., "lift up" message) is displayed on the display. The threshold period of time may be about 1 to about 10 seconds. In an implementation, the threshold period of time is 5 seconds.

At 2520, the system unit detects that the user has initially lifted the sheath, system unit, or both from the tissue. In an implementation, the lift is detected by determining that measured oximetry information is no longer valid for the patient tissue. Invalid oximetry information may be outside of a range of predetermined valid oximetry information. Invalid oximetry information may include an oxygen saturation measurement that provides an invalid result, for example, from an extreme property prediction, a poor fit of measured values to a lookup database of stored Monte Carlo simulated reflectance curves, ambient light saturation (e.g., when the system unit is lifted from tissue, or other factors.

When the system unit detects that a lift has occurred, the system unit then determines whether the lift occurred when the lift message was displayed. The system unit may then store the first oximetry information in a memory location in which the average oximetry information is stored. The system unit may also store information (e.g., the average count number) for a number of times oximetry information is stored for the average oximetry information. At the current step of the method, the number of stored pieces of oximetry information is one.

At 2525, the number of times that the oximetry information is stored for the average oximetry reading is displayed on the display. Referring to FIG. 21, the number of times that the oximetry information is stored for the average oximetry reading is 1. When the number of times that the oximetry information is stored is displayed on the display, the average oximetry information may also be displayed. If the number of times that the oximetry information is stored is 1, then the oximetry information is not an average, but is the first oximetry information. In an embodiment, the average oximetry information is not displayed (FIG. 21) on the display until a threshold number (e.g., three, FIG. 22) of pieces of oximetry information are averaged and stored in the memory. The information displayed may be two dashes or a different icon.

At 2530, the system unit detects that the second window of the sheath or the probe face of the probe tip of the system unit is placed back into contact with the patient tissue. The location on the patient tissue may be the first tissue location associated with step 2500 or may be a different tissue location (i.e., second tissue location). The system unit may then detect the contact with the patient tissue by generating valid oximetry information that is in the range of predetermined valid oximetry information.

At 2535, the system unit makes another oximetry measurement (e.g., a second oximetry measurement) of the patient tissue and generates additional oximetry information (e.g., second oximetry information) for the threshold period of time. The system unit may store the additional oximetry information in the system unit memory. The display of the system unit may display the oximetry information (e.g., oxygen saturation) that is determined by the system unit. In an implementation, the system unit does not display the oximetry information.

At 2540, after the oximetry measurement of step 2535 is performed for the threshold period of time, the use message (e.g., "lift up" message) is displayed on the display.

At 2545, the system unit detects that the user has lifted the sheath, system unit, or both from the tissue.

At 2550, if the system unit determines that the use message (e.g., "lift up") was displayed on the display when the sheath, system unit, or both are lifted from the tissue, the additional oximetry information (e.g., the second oximetry information) is added to the prior generated oximetry information (e.g., the first oximetry information) and is stored in the memory. The system unit may generate the average of the summed oximetry information. At the current step of the method, the first and second oximetry information are averaged and stored in the memory.

The system unit may also increment the stored information for the number of times oximetry information is stored for the average oximetry information. At the current step of the method, the number of stored pieces of oximetry information is two. If the sheath, system unit, or both are lifted from the tissue and placed onto the tissue for the threshold number of times (e.g., 3 times), then the system unit displays the average generated at 2555 on the display.

At 2550, if the system unit determines that the use message (e.g., "lift up") was not displayed on the display when the sheath, system unit, or both are lifted from the tissue, the addition oximetry information (e.g., the second oximetry information) is not averaged with the prior stored average oximetry information (e.g., the first oximetry information). That is, step 2555 is skipped. Additionally, the system unit displays the current average for the oximetry information on the display (2565).

At 2565, the method repeats method steps 2530 to 2565 until the user stops the method from executing, such as by inverting the system unit to reset the average oximetry information. For example, the number of times that the sheath, system unit, or both are lifted and placed onto the tissue may be reset to zero.

In an implementation, the method begins at 2525 and proceeds to step 2565 as described above, but the number of collected samples that is displayed on the display may be zero prior to a first oximetry measurement being taken at step 2535 and prior to oximetry information (e.g., an oxygen saturation value) being displayed on the display at step 2565.

In an implementation, the method begins at 2525 and proceeds to step 2565 as described above, but the number of collected samples that is displayed on the display may be one prior to the first oximetry measurement being taken at step 2535 and prior to first oximetry information (e.g., an oxygen saturation value) being displayed on the display at step 2565.

Figure 26:
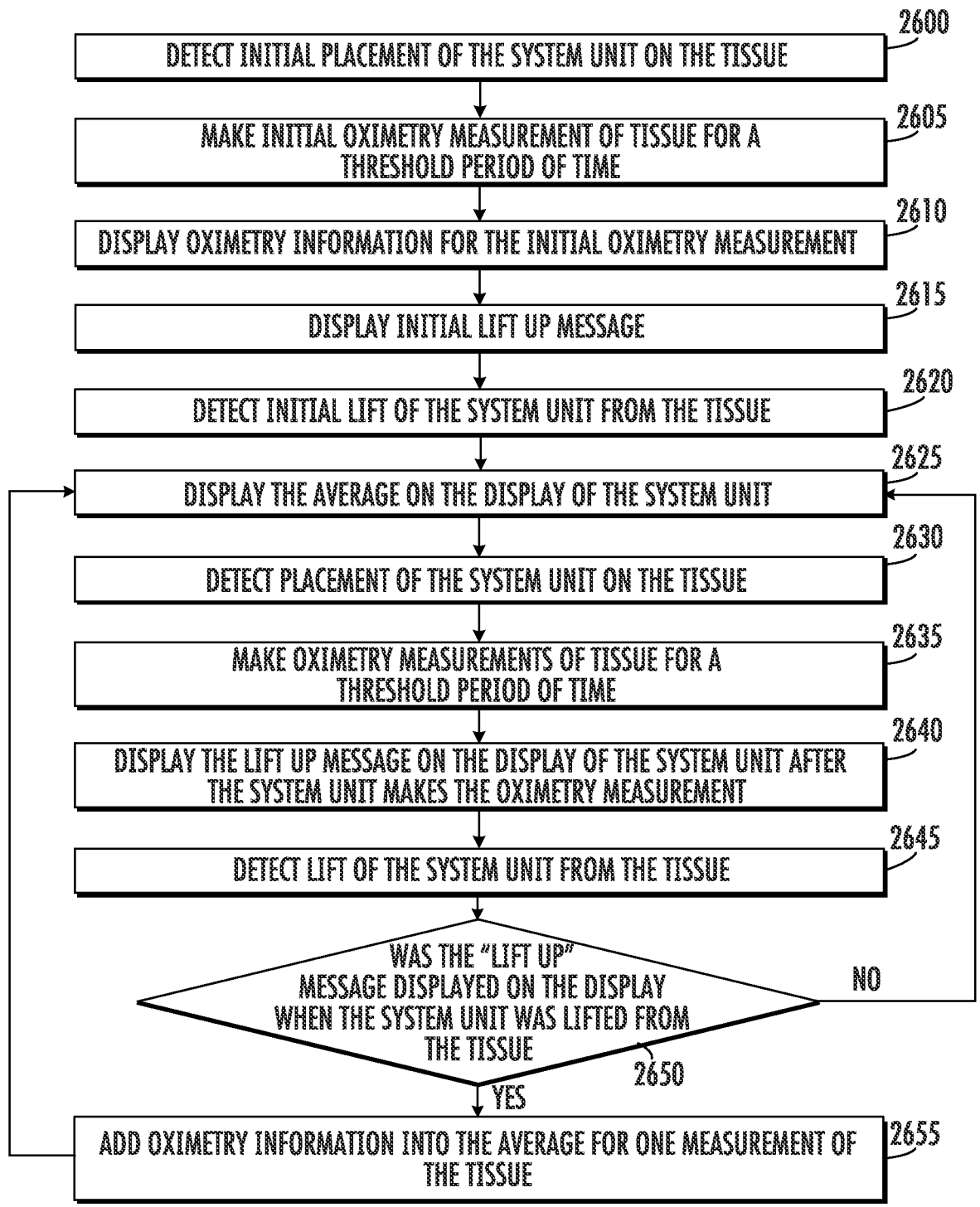
FIG. 26 is a flow diagram of a method of operation of the system unit for generating average oximetry information, in an implementation.

FIG. 26 is a flow diagram of a method of operation of the system unit for generating average oximetry information, in an implementation. The flow diagram shows an example embodiment in an implementation. Steps may be added, removed, or combined without deviating from the method.

At 2600, the second sheath window of the sheath or the probe face of the probe tip of the system unit (e.g., if used without the sheath) is initially placed into contact with patient tissue by a user at a first tissue location.

At 2605, the system unit makes a first oximetry measurement of the patient tissue and generates first oximetry information. The system unit may store the determined oximetry information in one of the memories of the system unit, such as the system unit RAM 312. This first oximetry information may be stored in a memory location in which the average oximetry information is stored.

At 2610, the display of the system unit displays the first oximetry information (e.g., oxygen saturation) that is determined by the system unit.

At 2615, after the first oximetry measurement is performed for a threshold period of time, the use message (e.g., "lift up" message) is displayed on the display. The threshold period of time may be about 1 to about 10 seconds. In an implementation, the threshold period of time is 5 seconds.

At 2620, the system unit detects that the user has initially lifted the sheath, system unit, or both from the tissue. In an implementation, the lift is detected by determining that measured oximetry information is no longer valid oximetry information for the patient tissue. Invalid oximetry information may be outside of a range of predetermined valid oximetry information.

When the system unit detects that a lift has occurred, determines that the lift occurred when the lift message was displayed, or both, the system unit may store the first oximetry information in a memory location in which the average oximetry information is stored. The system unit may also store information (e.g., a number) for a number of times oximetry information is stored for the average oximetry information. At the current step of the method, the number of stored pieces of oximetry information is one.

At 2625, the system unit displays the current average of the oximetry information on the display. The current average may be stored in a memory (e.g., RAM 312) of the system unit and retrieved from the memory for display on the display. If only a first oximetry measurement is taken at 2625, then the displayed oximetry information is for the first oximetry measurement (not an average for a number of lift ups and placements onto tissue) of the tissue. The display may also display the number of oximetry measurements in the current average of the oximetry information. For example, if only a first oximetry measurement is taken at 2625, then the number display is one (FIG. 21); if the first and second oximetry measurements are included in the average, then the number two is displayed; if the first, second, and third oximetry measurements are included in the average, then the number three is displayed; if the first, second, third, and fourth oximetry measurements are included in the average, then the number four is displayed; and the displaying of the numbers of the oximetry measurements included in the average oximetry measurement continues to be incremented for each additional oximetry measurement included in the average.

At 2630, the system unit detects that the second window of the sheath or the probe face of the probe tip of the system unit is placed back into contact with the patient tissue. The location on the patient tissue may be the first tissue location associated with step 2600 or may be a different tissue location (i.e., second tissue location). The system unit may then detect the contact with the patient tissue by generating valid oximetry information that is in the range of predetermined valid oximetry information.

At 2635, the system unit makes another oximetry measurement of the patient tissue and generates additional oximetry information for the threshold period of time. The system unit may store the additional oximetry information in the system unit memory. The display of the system unit may display the oximetry information (e.g., oxygen saturation) that is determined by the system unit. In an implementation, the system unit does not display the oximetry information.

At 2640, after the oximetry measurement of step 2635 is performed for the threshold period of time, the use message (e.g., "lift up" message) is displayed on the display.

At 2645, the system unit detects that the user has lifted the sheath, system unit, or both from the tissue.

At 2650, if the system unit determines that the use message (e.g., "lift up") was displayed on the display when the sheath, system unit, or both are lifted from the tissue, the addition oximetry information generated at 2635 is averaged with the prior stored average oximetry information (2655). The system unit may also increment the stored information for the number of times oximetry information is stored for the average oximetry information.

At 2650, if the system unit determines that the use message (e.g., "lift up") was not displayed on the display when the sheath, system unit, or both are lifted from the tissue, the addition oximetry information is not averaged with the prior stored average oximetry information. That is, step 2655 is skipped. Additionally, the system unit displays the current average for the oximetry information on the display (2625).

At 2655, the method repeats method steps 2625 to 2655 until the user stops the method from executing, such as by inverting the system unit to reset the average oximetry information. For example, the number of times that the sheath, system unit, or both are lifted and placed onto the tissue may be reset to zero.

In an implementation, the method begins at 2625 and proceeds to step 2655 as described above, but the displayed average at 2625 may be indeterminate before a first oximetry measurement is made by the system unit. After a first oximetry measurement is made by the system unit at 2635, the average may be the first oximetry measurement, after a second oximetry measurement is made by the system unit at 2635, the average may be the average of the first and second oximetry measurements, after a third oximetry measurement is made by the system unit at 2635, the average may be an average of the first, second, and third oximetry measurements. The series of extending the average to include additional oximetry measurements may continue with fourth, fifth, sixth, seventh, eighth, ninth, or more oximetry measurements. The number that is stored for the number of oximetry measurements for the average may be zero at 2625 before a first oximetry measurement is made. The number that is stored for the number of oximetry measurements for the average may be one at 2625 before a first oximetry measurement is made. The system unit may retrieve this number from memory to determine that no valid average oximetry information has been generated. The system unit may display bars, another icon, zero, nothing, or another indicator to indicate that a first oximetry measurement has not yet been made.

Figure 27:
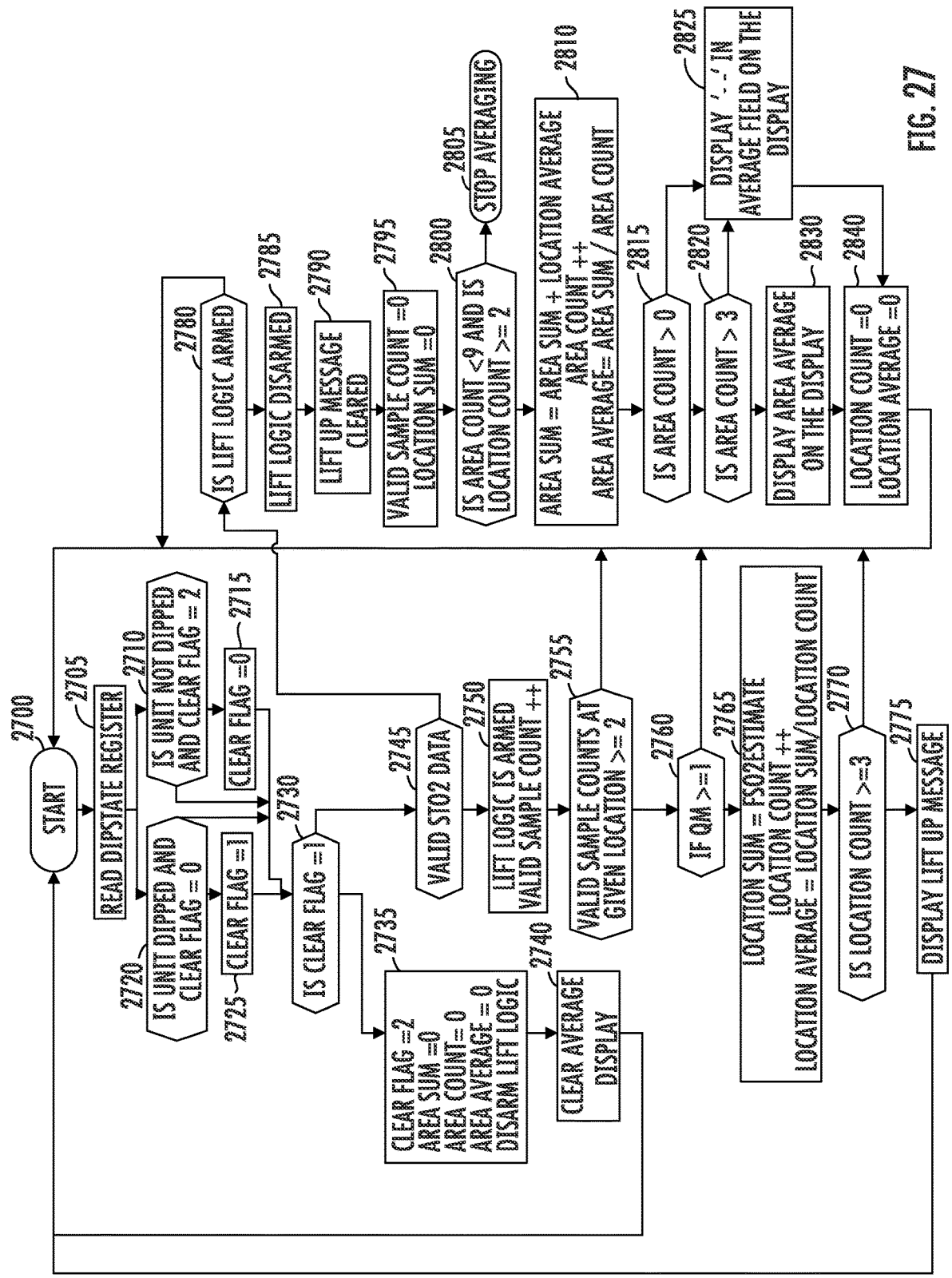
FIG. 27 is a flow diagram of a method of operation of the system unit for generating average oximetry information, in an implementation.

FIG. 27 is a flow diagram of a method of operation of the system unit for generating average oximetry information, in an implementation. The flow diagram shows an example embodiment in an implementation. Steps may be added, removed, or combined without deviating from the method.

At 2700, the second sheath window of the sheath or the probe face of the probe tip of the system unit (e.g., if used without the sheath) is initially placed into contact with patient tissue by a user at a first tissue location. In an implementation, at 2700 valid oximetry measurements have been made by the system unit (e.g., valid oxygen saturation measurement are made), and the time since the last oximetry measurement has been made is greater than 2 seconds (e.g., time_now−last_StO2updatetime>2 seconds).

At 2705, the system unit reads the dipstate register to determine the inversion state (inverted or not inverted) of the system unit.

At 2710, if the system unit is not dipped (e.g., not inverted) and the clear flag for the dip state is 2 (system unit has been changed from inverted to not inverted), then the clear flag is set to zero (normal operation for system unit) at 2715. If the system unit is not dipped (e.g., not inverted) and the clear flag for the dip state is 0 (normal operation state), then the system unit determines whether the clear flag is one at 2730.

At 2720, the system unit determines whether the system unit is dipped (e.g., inverted) and the clear flag is zero. If the system unit is dipped (e.g., inverted) and the clear flag is zero, then the clear flag is set to one (system unit has been changed from not inverted to inverted) at 2725. If the system unit is dipped (e.g., inverted) and the clear flag is not zero, then the system unit determines whether the clear flag is one at 2730.

If the clear flag is one at 2730, then the average information for the tissue locations is reset. Specifically, the clear flag is set to two, the sum for the average for the tissue locations is set to zero, the average count for the tissue locations is set to zero, the average for the tissue location is set to zero, and the lift logic for the system unit is disarmed. That is, the system unit is not configured to determine whether the system unit has been lifted from patient tissue.

At 2740, the average displayed on the display of the system unit is cleared, and the method returns to the start state 2700 to generate a new oximetry measurement average.

If the clear flag is not one at 2730, then the system unit makes an oximetry measurement (e.g., an oxygen saturation measurement) and determines whether oximetry information generated from the oximetry measurement is valid at 2745. The system unit may display the oximetry information on the display of the system unit if the oximetry information is valid. If the the oximetry information is not valid, then at 2780 the system unit determines if the lift logic is armed. The lift logic is armed if the system unit displays the use message (e.g., "lift up") on the display and monitors for the sheath or system unit from being lifted from the tissue. Steps taken at 2780 and after are described further below.

At 2750, the system unit determines whether the lift logic is armed and increments the sample count for the tissue location by one.

At 2755, the system unit determines whether the valid sample count for tissue being measured is greater than or equal to 2. If the system unit determines that the valid sample count for tissue being measured is not greater than or equal to 2, then the system unit returns to the start at 2770.

If the system unit determines that the valid sample count for tissue being measured is greater than or equal to 2, then at 2760 the system unit determines whether the quality measurement (QM) of the oximetry measurements for the tissue being measured is greater than or equal to 1. The QM is greater than or equal to one, if the oximetry measurement information is valid. If the QM is not greater than or equal to one, then the system unit returns to the start at 2770. If the QM is greater than or equal to one, then at 2765 the sum for the number of measurements taken ("location sum") for the tissue being measure is set to the oximetry measurement for the tissue ("location sum=fSo2estimate"), the measurement count for the tissue being measured is incremented by one ("location count++"), and the oximetry measurement average for the tissue being measured is calculated ("location average=location sum/location count") where the location sum include the sum of the oximetry measurement information (e.g., oximetry measurement values) for the tissue location include the latest oximetry information (e.g., latest oximetry measurement value) for the latest tissue location.

At 2770, the system unit determines whether the measurement count for the tissue being measured is greater than or equal to 3. If the measurement count for the tissue being measured is not greater than or equal to 3, then at 2780 the system unit determines if the lift logic is armed. Steps taken at 2780 and after are described further below. If the measurement count for the tissue being measured is greater than or equal to 3, then at 2775 the system unit displays the use message (e.g., "lift up") on the display of the system unit. After the lift message is displayed, the system unit returns to the start state of the method at 2700.

At 2780, if the system unit determines that the lift logic is not armed, then the system unit returns to the start at 2770. if the system unit determines that the lift logic is not armed, then at 2785 the lift logic is disarmed. That is, the system unit does not attempt to determine whether the sheath or system unit has been lifted from the tissue being measured.

At 2790, the use message (e.g., "lift up) is removed from the display.

At 2795, the sample count is set to zero, and the location sum is set to zero.

At 2800, the system unit determines whether the area count (e.g., the number of tissue locations of a patient that are measured) is less than 9 and whether the location count (e.g., number of oximetry measurements made for a tissue location) is greater than or equal to 2. If the area count is not less than 9 and if the location count is not greater than or equal to 2, then the system unit stops generating an average value for the oximetry measurements, at 2805.

If the area count is less than 9 and if the location count is greater than or equal to 2, then the system unit calculates the sum of the oximetry measurements for each of the tissue locations (i.e., "area sum=area sum+location average"), at 2810. The area count is incremented by one, at 2810. And, the average oximetry measurement for the tissue location is calculated (i.e., "area average=area sum/area count"), at 2810.

At 2815, the system unit determines whether the area count (number of tissue locations of the patient for which oximetry measurements are made) is greater than to zero. If the area count is not greater than or equal to zero, then the system unit does not display the area average until three tissue locations have been measured (e.g., oximetry measurement made) by the system unit, at 2825 (FIG. 21). Instead of displaying the are average, the system unit may display text (e.g., two dashes, "--"), an icon, or both to indicate that the area average is not being displayed. If the area count is not greater than to zero, then the system unit proceeds to 2820.

Figure 22:
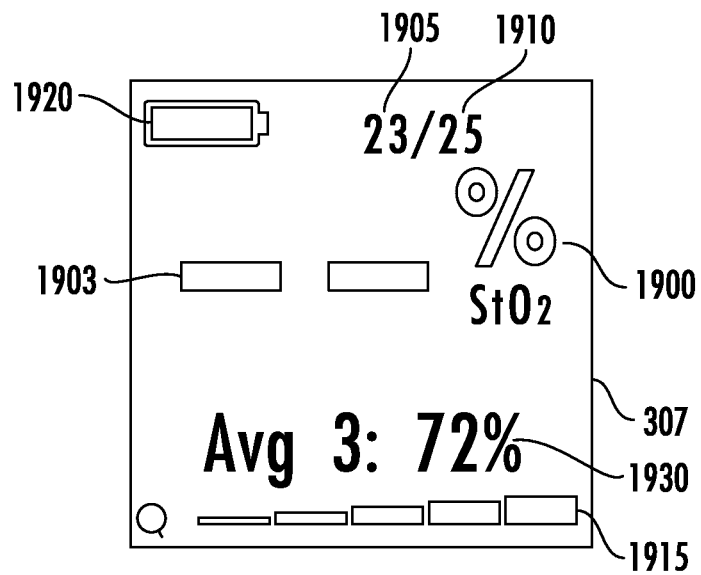

At 2820, the system unit determines whether the area count (number of tissue locations of the patient for which oximetry measurements are made) is greater than three. If the area count is not greater than three, then the system unit displays the area count on the display, and does not display the area average at 2825. That is, the system unit does not display the area average until three tissue locations have been measured (e.g., oximetry measurement made) by the system unit (FIG. 21). Instead of displaying the are average, the system unit may display text (e.g., two dashes, "--"), an icon, or both to indicate that the area average is not being displayed. If the area count is greater three, then at 2830, the system unit displays the area count on the display, and displays the area average (FIG. 22).

At 2840, the location count is set to zero and the location average is set to zero. The system unit then returns to the start of the method at 2700. That is, after a pass through the method the system unit may continue to make oximetry measurements for tissue locations of the patient tissue to generate an average of the tissue location for which valid oximetry measurements are made.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
providing a device comprising a top housing comprising a display visible from an exterior of the top housing; and a bottom housing comprising a printed circuit board, a processor formed on the printed circuit board, a probe tip coupled to the processor, and a first wall, wherein the first wall comprises a front side surface, a back side surface, and an opening extending from the front side surface to the back side surface, the printed circuit board is coupled to the front side surface of the first wall, the printed circuit board comprises a first plurality of electrical contacts located on the back side surface and coupled to the processor, the electrical contacts on the back side surface of the printed circuit board are visible through the opening formed in the first wall of the bottom housing, the back side surface of the first wall comprises a first riser that extends from the back side surface of the first wall, the first riser comprises a sidewall, an angle between at least a portion of the sidewall of the first riser and the back side surface of the first wall that is less than a straight angle;
making, by the device, a plurality of oximetry measurements for a plurality of tissue locations;
generating a plurality of instantaneous oximetry values based on the plurality of oximetry measurements for the plurality of tissue locations; generating an average of the oximetry values; and
displaying simultaneously on the display at least one of the instantaneous oximetry values with the average value.

2. The method of claim 1 wherein the plurality of tissue locations includes a first tissue location and a second tissue location.

3. The method of claim 2 wherein the plurality of instantaneous oximetry values includes at least a first instantaneous oximetry value for the first tissue location and at least a second instantaneous oximetry value for the second tissue location.

4. The method of claim 3 wherein the first and second tissue locations are different tissue locations.

5. The method of claim 3 wherein the at least first instantaneous oximetry value is for the first tissue location, and the at least second instantaneous oximetry value for the second tissue location.

6. The method of claim 5 wherein the at least one of the instantaneous oximetry values is the at least second instantaneous oximetry value for the second tissue location.

7. The method of claim 6 wherein the average value is an average of the at least first and second instantaneous oximetry values.

8. The method of claim 7 wherein the back side surface of the first wall comprises a second riser that extends from the back side surface of the first wall, the second riser comprises a sidewall, an angle between at least a portion of the sidewall of the second riser and the back side surface of the first wall is less than a straight angle.

9. The method of claim 7 wherein the back side surface of the first wall comprises a third riser that extends from the back side surface of the first wall, the third riser comprises a sidewall, an angle between at least a portion of the sidewall of the third riser and the back side surface of the first wall is less than a straight angle.

10. The method of claim 9 wherein the portions of the sidewalls of the first, second, and third risers face the same direction.

11. The method of claim 10 wherein the display is located at a proximal end of the device and the probe tip is distal from the proximal end at a distal end of the device, and the direction is away from the distal end.

12. The method of claim 7 wherein the device comprises a detachable battery coupled to the back side surface of the of the first wall, the battery comprises a sidewall and a first pocket formed in the sidewall, wherein the sidewall of the battery faces the back side surface of the first wall of the bottom housing,
the first riser is at least partially located in the first pocket, and the first pocket comprises a sidewall that is coupled to the portion of the sidewall of the first riser.

13. The method of claim 12 wherein the battery comprises a second plurality of electrical contacts, the first and second plurality of electrical contacts are coupled.

14. The method of claim 13 wherein the first and second pluralities of electrical contacts each includes a power connector and a data connector.

* * * * *